(12) United States Patent
Toreki et al.

(10) Patent No.: US 7,790,217 B2
(45) Date of Patent: Sep. 7, 2010

(54) METHOD OF ATTACHING AN ANTIMICROBIAL CATIONIC POLYELECTROLYTE TO THE SURFACE OF A SUBSTRATE

(75) Inventors: William Toreki, Gainesville, FL (US); Bernd Liesenfeld, Gainesville, FL (US); David Moore, Gainesville, FL (US); Susan Leander, Gainesville, FL (US); Christopher Batich, Gainesville, FL (US)

(73) Assignees: Quick-Med Technologies, Inc., Gainesville, FL (US); University of Florida Research Foundation, Inc., Gainesville, FL (US)

( * ) Notice: Subject to any disclaimer, the term of this patent is extended or adjusted under 35 U.S.C. 154(b) by 612 days.

(21) Appl. No.: 11/569,942

(22) PCT Filed: Aug. 22, 2006

(86) PCT No.: PCT/US2006/032955

§ 371 (c)(1),
(2), (4) Date: Dec. 1, 2006

(87) PCT Pub. No.: WO2007/024974

PCT Pub. Date: Mar. 1, 2007

(65) Prior Publication Data

US 2009/0181157 A1    Jul. 16, 2009

Related U.S. Application Data

(60) Provisional application No. 60/710,127, filed on Aug. 22, 2005.

(51) Int. Cl.
*B05D 3/02* (2006.01)

(52) U.S. Cl. .............. 427/2.31; 427/8; 427/385.5; 427/389.9; 427/391; 427/392; 427/394; 427/395; 427/396

(58) Field of Classification Search ............... None
See application file for complete search history.

(56) References Cited

U.S. PATENT DOCUMENTS

| | | | | |
|---|---|---|---|---|
| 5,084,096 A * | 1/1992 | Stovicek | ................ | 106/18.21 |
| 5,830,526 A * | 11/1998 | Wilson et al. | ................ | 427/2.1 |
| 6,039,940 A * | 3/2000 | Perrault et al. | ............ | 424/78.06 |
| 6,200,354 B1 * | 3/2001 | Collins et al. | ................ | 8/554 |
| 6,326,323 B1 * | 12/2001 | Shimano et al. | .......... | 428/32.16 |
| 6,749,641 B2 * | 6/2004 | Cates et al. | ................ | 8/115.51 |
| 6,797,856 B1 * | 9/2004 | Kolb et al. | ................ | 604/360 |
| 6,960,371 B2 * | 11/2005 | Bunyard et al. | ............ | 427/342 |
| 2002/0177828 A1 * | 11/2002 | Batich et al. | ................ | 604/367 |
| 2003/0050589 A1 * | 3/2003 | McDevitt et al. | ............ | 602/41 |
| 2003/0163073 A1 * | 8/2003 | Effing et al. | ................ | 602/48 |
| 2004/0009210 A1 * | 1/2004 | Koenig et al. | ............... | 424/445 |
| 2004/0031749 A1 * | 2/2004 | Koslow | ................ | 210/505 |
| 2004/0149572 A1 * | 8/2004 | Schlenoff et al. | ........... | 204/296 |
| 2005/0033251 A1 * | 2/2005 | Toreki et al. | ................ | 604/367 |
| 2006/0010619 A1 * | 1/2006 | Hees et al. | ..................... | 8/445 |

FOREIGN PATENT DOCUMENTS

| | | | |
|---|---|---|---|
| JP | 58-143749 A | | 8/1983 |
| JP | 07-268780 | * | 10/1995 |
| JP | 10-182311 | | 7/1998 |
| WO | 2004/076770 A1 | | 9/2004 |

* cited by examiner

*Primary Examiner*—Erma Cameron
(74) *Attorney, Agent, or Firm*—Gerry J. Elman; Elman Technology Law, P.C.

(57) ABSTRACT

A method of bonding an antimicrobial cationic polyelectrolyte to the surface of a substrate is described, wherein the antimicrobial thus attached to the substrate provides the substrate with antimicrobial properties, and at least a portion of the bonded antimicrobial is substantially non-leachable during normal conditions of use and storage. A method of manufacturing an antimicrobial material is described which comprises exposure of the substrate to a solution of antimicrobial cationic polyelectrolyte, followed by drying the exposed substrate thoroughly to impart a non-leaching property to at least a portion of the antimicrobial cationic polyelectrolytes.

31 Claims, No Drawings

METHOD OF ATTACHING AN ANTIMICROBIAL CATIONIC POLYELECTROLYTE TO THE SURFACE OF A SUBSTRATE

FIELD OF THE INVENTION

The invention relates to methods of manufacture of inherently antimicrobial materials.

BACKGROUND ART

Reduction or elimination of microorganisms on surfaces is important in a broad variety of applications. One approach to interfere with the ability of microorganisms to survive on various materials is to modify the surface of those materials by attachment of antimicrobial agents.

Deciding how best to attach an antimicrobial agent to a material is guided, at least in part, by the planned end-use of the material. One important and useful consideration is that the antimicrobial activity be persistent. This may be achieved by permanently attaching the antimicrobial agent to the surface, so that it is unable to migrate or leach away from the modified material surface when the modified material is exposed to fluids. For example, for applications in which the modified material will come into contact with aqueous fluids, it is important that the antimicrobial agent is not rinsed away when the modified material comes into contact with aqueous fluids. For applications in which the modified material will come into contact with aqueous biological fluids, it is important that the antimicrobial agent is not rinsed away, or otherwise inactivated, when the modified material is exposed to aqueous biological fluids. For applications in which the modified material is to be used repeatedly, it is important that the antimicrobial agent is not washed or rinsed away when the modified material is washed or rinsed in fluids in between repeated uses. An additional consideration in the development of approaches intended to meet the needs of these and related applications, is that some microorganisms have been found to possess the ability to develop resistance to certain antimicrobial agents, such as antibiotics or silver. Currently available approaches do not adequately address all of these considerations.

By their design, approaches utilizing leachable active agents (such as triclosan, silver compounds, or biguanides) to impart antimicrobial activity to materials suffer from eventual depletion or loss of the antimicrobial activity conveyed by the leachable active agents. Depletion or loss of antimicrobial activity can occur especially when the materials come into incidental contact with fluids, or during intentional contact with fluids during washing or rinsing procedures employed between repeated uses of the modified material. In addition, the leaching of certain active agents may prohibit or limit the use of these approaches in applications where the leaching of the active agent will cause undesired consequences (e.g. leaching into open wounds, leaching onto products intended for human consumption, and staining of skin).

One example of an approach utilizing a potentially leachable active agent is Burba et al. (U.S. Pat. No. 5,154,932), which discloses a method for providing antimicrobial activity to a formulation or product which have negative surface charges, effective for deactivating microorganisms, said method comprising adding to the formulation or product an amount of a positively charged layered crystalline mixed metal hydroxide sufficient to impart antimicrobial activity to the formulation or product.

Another example of an approach utilizing a potentially leachable active agent is Lyon et al. (U.S. Pat. No. 6,042,877), which discloses a method of making an antimicrobial article comprising providing a substrate, forming a solution comprising a chelating polymer and a metal ion, depositing the solution on the substrate, drying the substrate to form a coated substrate, and adding a potentiator to the coated substrate to form the antimicrobial article.

Other approaches have employed methods that attach silane-based quaternary ammonium compounds to particular substrates via a siloxane bond. For example, AEGIS Environments' product line includes products that utilize polymers of 3-(trimethoxysilyl)propyldimethyl octadecyl ammonium chloride. According to product literature, AEM 5700 is 43% 3-(trimethoxysilyl) propyldimethyloctadecyl ammonium chloride in methanol, which can be used to coat the surface of textiles. This is not a polymeric compound; although, some interlinking of the applied silane may occur after application to the substrate. These types of materials tend to impart a hydrophobic character to the substrates, and are thus less than suitable for many applications. Also, the hydrolytic instability caused by the bulky (C18 quat) substituent on the siloxane tends to make the materials prone to lose their antimicrobial activity.

Another example utilizing silane-based quaternary ammonium compounds is Blank et al. (U.S. Pat. No. 5,035,892), which discloses a method of inhibiting the proliferation of potentially destructive microorganisms on a substrate comprising treating the substrate with an effective amount of an antimicrobial superabsorbent composition formed of a crosslinked hydrophilic sodium salt form of a partially neutralized acrylic acid based polymer gel, the polymer gel having covalently bonded thereto an organosilane, the organosilane being present in an amount to prevent hydrophobing and reduction of the absorbent capacity of the polymer gel. Unfortunately, in practice, the amount of organosilane must often be reduced to below a desirable antimicrobially efficacious level in order to prevent the aforementioned hydrophobing. Another example is Blank (U.S. Pat. No. 4,847,088), which discloses a method of inhibiting the proliferation of potentially destructive microorganisms on a substrate comprising treating the substrate with an effective amount of the synergistic antimicrobial composition comprising a mixture of (a) an organosilane; and (b) an acid. Again, this example uses siloxanes as described above.

The silane-based quaternary ammonium systems suffer from other drawbacks as well. The long alkyl chains used (typically C-18) tend to make the treated material hydrophobic—not a desirable property for an absorbent material such as a wound dressing. Additionally, it has been found that the silane-quats are deactivated in the presence of blood or other proteinaceous material (see EP 0136900).

Another example is Shiau et al. (U.S. 010043938 A1), which discloses a process for producing an antimicrobial article comprising (a) dissolving a predetermined amount of quaternary ammonium organosiloxane salt in water; to make a solution of about 0.05 to 20 wt. % of the salt, (b) mixing a ground calcining aid with a solvent to make a solution, wherein said calcining aid to solvent ratio is from 1:1 to 1:10, (c) soaking a preformed honeycomb-shaped substrate into the solution of the aforesaid step b; followed by drying and calcining at 400-1500° C., (d) impregnating the calcined honeycomb-shaped substrate with the salt solution of the aforesaid steps a and e, drying the impregnated substrate at 50° to 200° C. These excessive temperatures (400° to 1500° C.) are clearly unsuitable for common substrates such as cellulose and polymers.

These shortcomings have been overcome, in part, by Batich in U.S. Pat. No. 7,045,673 and application U.S. Ser. No. 020177828 A1. The materials and methods described in those references teach that an antimicrobial material can be prepared by graft polymerization of an antimicrobial quaternary ammonium monomer onto a substrate such as cellulose. Still, that method has limitations and shortcomings. Namely, it requires a vinyl polymerization step which must be conducted under an oxygen-free atmosphere, which is a costly restriction to commercial development. Furthermore, the process described therein is wasteful in terms of utilization of antimicrobial cationic polyelectrolyte (for two reasons). First, a large excess of polymerizable quaternary ammonium compound must be utilized, and most of that is not incorporated into the final product. Second, the required grafting levels (up to more than 40% antimicrobial "add-on") are at least an order of magnitude greater than is required by the present invention, in order to obtain the same level of antimicrobial efficacy. These shortcomings are discussed further elsewhere in the current application.

Lin describes ("*Mechanism of Bactericidal and Fungicidal Activities of Textiles Covalently Modified with Alkylated Polyethyleneimine*" Biotechnology and Bioengineering v83(2), p168-172, Jul. 20, 2003) a process for covalently attaching hydrophobic polycations to woven textiles using a six-step process that requires various organic solvents and long processing times. The observed microbicidal activity indicated a range of 88% to 99% reduction for various organisms. The process described by the current application is shorter, faster, safer, and more economical than the process described by Lin. In addition, the material produced by the method of the current invention is orders of magnitude more effective in reducing the microbial activity, and is not hydrophobic. The shortcomings of the method described by Lin are cited in the following reference: Daewon Park, Jun Wang, and Alexander M. Klibanov, "*One-Step, Painting-Like Coating Procedures To Make Surfaces Highly and Permanently Bactericidal*" Biotechnol. Prog. 22, p584-589 (2006). A similar process was used by Lee (Biomacromolecules 5 p877-883 (2004)).

Abel ("*Preparation and investigation of antibacterial carbohydrate-based surfaces*" Carbohydrate Research 337 (2002) p2495-2499) describes the covalent attachment of low molecular weight (non-polymeric) quaternary ammonium moieties to cellulose substrates. Like the methods of Lin and Lee, Abel's method is a multistep process which requires the use of hazardous and/or flammable organic reagents and solvents such as p-toluenesulfonylchloride, pyridine, and acetonitrile.

BacStop™ is sold as a fabric sanitizer by Edmar Chemical Company (Cleveland, Ohio). The product contains 50% didecyldimethylammonium chloride (DDDMAC). It is designed to be added to the final rinse cycle of a laundering process. BacStop™ is claimed to reduce bacterial count by 99.9% (3-log reduction) for *Staph. aureus* and *Klebsiella pneumoniae*, and to impart a residual bacteriostatic finish to fabrics. Such a residual effect is not unexpected, in that several rinses with fresh water would be needed for full removal of just about any soluble chemical from a fabric to which it has been applied. The active ingredient (DDDMAC) is a non-polymeric quaternary ammonium compound. The BacStop™ product label does not claim a residual antimicrobial property for fabrics that have been treated with the product—only a residual bacteriostatic property is claimed. It is demonstrated in comparative examples presented below that monomeric quaternary ammonium compounds such as DDDMAC are not effective in the practice of the current invention, as they do not produce a non-leaching bond with a substrate to give an inherently antimicrobial material with a desirable degree of antimicrobial efficacy.

Senka, in JP 09078785 describes some of the shortcomings of silane-based quaternary ammonium antimicrobials for the preparation of inherently antimicrobial materials (such as those described by Blank—see above). Senka teaches that an antimicrobial coating can be formed on non-celluosic substrates using a copolymer of a quaternary ammonium compound and acrylic acid derivatives. The copolymer has the property that it is soluble in aqueous solution; however, once the solution is dried, the resulting dried solid polymer becomes insoluble. Such behavior can be described as "self-crosslinking" in that the polymer (or copolymer) spontaneously crosslinks upon drying. Thus, a solution of the copolymer can be applied to a substrate and after drying an insoluble coating with antimicrobial properties is produced. Because the formation of the coating does not depend on interactions between the substrate and the coating, it is possible to apply this coating to inert substrates such as synthetic polymers. One skilled in the art would realize that these coatings are expected to be flexible when wet, or sufficiently hydrated; however, they would be expected to be stiff and brittle when dried. This is likely to cause undesirable changes in the physical properties of the material, such as stiffness, feel or hand. It is also likely that distortion, stretching, or folding of the underlying substrate would likely cause the dry coating to fall apart and detach from the substrate, particularly since there is no specific bonding between the coating and substrate. The dried copolymer presumably has become crosslinked due to interaction of the positively-charged quaternary components and the acrylic acid derived components, which are expected to be negatively-charged at neutral pH. Interaction of the oppositely-charged components of the copolymer is also likely to cause some screening of the positive charge provided by the quaternary component, and resulting in a reduction of antimicrobial efficacy. Furthermore, the simple fact that the coating consists of another component in addition to the quaternary component necessarily dilutes the charge density provided by the quaternary component, and thus also will reduce the ultimate antimicrobial effect compared to a polymer that consists of 100% quaternary component. These shortcomings are discussed further below.

In general, coatings are not a desirable approach to modification of cellulosic substrates such as textiles and wound dressings. While some coatings may form a very strong bond with a substrate, the attractive forces responsible for a robust and useful coating are generally between components of the coating (within the coating itself) rather than between the coating and the substrate. Coatings are generally somewhat thick (like paints, for instance), and can drastically affect the surface properties of textiles or other substrates. This can happen, for instance, by blocking or filling-in of porosity, or cementing-together of individual fibers. Additionally, some coatings require a curing step after application, in order to prevent subsequent dissolution.

Sawan (U.S. Pat. No. 6,264,936) describes an antimicrobial material which can be used to form on the surface of a substrate an antimicrobial coating or layer which kills microorganisms on contact. The antimicrobial coating or layer, characterized in the reference as "non-leaching," is a combination of an organic matrix immobilized on the surface of the substrate to having biocidal metallic materials associated with the matrix. When a microorganism contacts the coating or layer, the biocidal metallic material is transferred to the microorganism in amounts sufficient to kill it. Specifically, the metallic antimicrobial agent used is silver. Although this method purports to provide a "non-leachable" coating, the mere fact that the metallic antimicrobial agent "is transferred" to the microorganism is contrary to the common definition of non-leachable. Furthermore, it is known that although silver and silver salts have very low solubility, the mechanism of antimicrobial activity is dependent on a finite solution concentration of silver ions. Indeed, Sawan later (column 3, line 9) qualifies the above statement to read "substantially low leachables". In a preferred embodiment of Sawan's patent, the organic material comprises a polyhexamethylene biguanide polymer which is crosslinked with an epoxide, such as N,N-bismethylene diglycidylaniline, to form a crosslinked network or matrix. This crosslinking step is necessary to prevent dissolution of the matrix. The materials described by Sawan generally require a curing step, generally in the range of 80° to 120° C., which is unsuitable for many substrates, particularly human skin. Furthermore, the preferred organic matrix polymer (polyhexamethylene biguanide) is known to be toxic to human cells in high concentrations (see U.S. Pat. No. 6,369,289 B1). The use of silver as an antimicrobial agent also incurs some undesirable effects. One disadvantage to this approach is that certain bacteria have been able to develop resistance to silver. (Silver S., "*Bacterial silver resistance: molecular biology and uses and misuses of silver compounds.*" FEMS Microbiology Reviews. 2003; 27:341-353). Another disadvantage to this approach is that diffusing silver may be able to enter the wound and may potentially stain the skin. An additional disadvantage of silver is the high cost of the raw material. Similar approaches are described in U.S. Pat. Nos. 6,180,584; 6,126,931; 6,030,632; 5,869,073, 5,849,311; and 5,817,325.

Brown (EP 0136900) describes a nonwoven fabric with antimicrobial properties for use as a surgical drape. This is produced by treatment of a rayon or woodpulp material with a binder and polyhexamethylene biguanide (PHMB). Because the applied PHMB is extractable by aqueous fluids, the amount of PHMB must be kept below a critical level, in order to prevent the leached PHMB from reaching toxic levels.

Payne, in U.S. Pat. No. 5,700,742, describes treatment of textile materials with combinations of PHMB and a strong acid in order to overcome problems such as discoloration, loss of antimicrobial efficacy, and undesirable changes to substrate properties that are associated with treatment of textiles using PHMB without the added strong acid.

Orr (U.S. Pat. No. 6,369,289 B1) teaches the use of PHMB in cellulosic wound dressings. Orr teaches that leachable PHMB can lead to adverse effects such as skin disorders, redness, tenderness and hives, but that these are avoided by utilizing a precisely-controlled amount to PHMB in the wound dressing. Non-leaching of the applied antimicrobial is not demonstrated or even suggested. Orr merely teaches that the amount of leachable PHMB is less than that which would cause irritation to skin or an open wound; however he provides no data to this effect, or that the materials provide useful antimicrobial efficacy at the level of PHMB used. In fact, Orr calculates the amount of PHMB applied to the dressing "by extraction", which necessarily implies that the materials can be leached or extracted. The use levels of PHMB cited by Orr are only slightly below those claimed by Brown (EP 0136900).

The method of Orr (U.S. Pat. No. 6,369,289 B1) is used to produce a commercial antimicrobial wound dressing known as "Kerlix-AMD", which contains 0.2% PHMB. The Kerlix-AMD dressing is known to show a distinct zone-of-inhibition (ZOI) in a Kirby-Bauer test (see Kerlix-AMD product brochure available at (http://www.kendallhq.com/catalog/brochures/KerlixSS.pdf). A measurable ZOI is a definite indicator of leachable antimicrobial activity. The antimicrobial effectiveness of Kerlix-AMD has been described "*Effectiveness of a New Antimicrobial Gauze Dressing as a Bacterial Barrier*" A. M. Reitsma, et al., University of Virginia Health System, Charlottesville, Va. This study makes no mention of non-leachable properties.

PHMB has been studied as an antimicrobial treatment for cotton fabric ("*Testing the Efficacy of polyhexamethlylene Biguanide as an Antimicrobial Treatment for Cotton Fabric,*" Michelle Wallace, AATCC Review, p18-20, November, 2001). Antimicrobial efficacy was maintained after laundering; however, no discussion of leaching is given; however, the data does show that antimicrobial efficacy diminishes with repeated laundering cycles. Presumably, this is due to loss of PHMB from the substrate (leaching).

Consequently, there exists a need for a method that can attach an effective and non-leaching amount of antimicrobial agent to a variety of substrate materials in a convenient, reliable, and cost-effective manner. The inadequacies of existing approaches are overcome with the present inventive method wherein an improved method of non-leachably attaching antimicrobial agents to a variety of substrate materials is provided.

SUMMARY OF THE INVENTION

Industrial Applicability

It is an aspect of this invention to provide a method of manufacturing an inherently antimicrobial absorbent material. The method establishes the attachment of non-leaching antimicrobial cationic polyelectrolytes to substrates, thereby imparting to the substrates an inherent non-leaching antimicrobial property, and not causing unwanted side-effects such as making the material hydrophobic (water repellent). The method of manufacturing an inherently antimicrobial material includes exposing the substrate to an aqueous solution of antimicrobial cationic polyelectrolytes, followed by drying the exposed substrate thoroughly to impart a non-leaching property to at least a portion of the antimicrobial cationic polyelectrolytes.

It is an aspect of the current invention to provide a method of manufacturing an inherently antimicrobial material comprised of a sufficient number of polymeric diallyldimethylammonium chloride molecules, non-leachably attached to a substrate comprised in whole or in part of a celluosic material, to render the material antimicrobial and non-hydrophobic, before, during, and after exposure of the material to aqueous fluids, said method comprising; loading the substrate with said polymeric diallyldimethylammonium chloride molecules by exposing the substrate to an aqueous solution of said polymeric diallyldimethylammonium chloride molecules, and thoroughly drying the loaded substrate to impart a non-leaching property to at least a portion of said polymeric diallyldimethylammonium chloride molecules.

It is an aspect of the current invention to provide a method of manufacturing an inherently antimicrobial material comprised of a sufficient number of antimicrobial cationic polyelectrolytes, non-leachably attached to a substrate, to render the material antimicrobial and nonhydrophobic, before, during, and after exposure of the material to aqueous fluids, said method comprising; loading the substrate with said antimicrobial cationic polyelectrolytes by exposing the substrate to an aqueous solution of said antimicrobial cationic polyelectrolytes, and thoroughly drying the loaded substrate to impart a non-leaching property to at least a portion of said antimicrobial cationic polyelectrolytes.

It is an aspect of this invention to provide a method of attaching an antimicrobial cationic polyelectrolyte to a substrate wherein said substrate is comprised in whole or in part of cellulose, and wherein said antimicrobial cationic polyelectrolyte is not self-crosslinking and has an average degree of polymerization of at least 3, wherein said method comprises the steps of wetting the substrate with an aqueous solution of the antimicrobial cationic polyelectrolyte followed by thoroughly drying of the wetted substrate, wherein said drying causes at least a portion of the antimicrobial cationic polyelectrolyte to become attached to the substrate in a non-leachable manner, and wherein the attached antimicrobial cationic polyelectrolyte provides an antimicrobial effect to the resulting product.

It is an aspect of this invention to provide a method of imparting non-leachable antimicrobial properties to a substrate wherein said substrate is comprised in whole or in part of cellulose, and wherein said non-leachable antimicrobial properties result from strong attractive interactions between said substrate and an applied antimicrobial cationic polyelectrolyte wherein said strong attractive interactions are caused to occur by thoroughly drying of the substrate after application of an aqueous solution of said antimicrobial cationic polyelectrolyte to the substrate.

It is an aspect of the current inventive method to provide a method of manufacturing an inherently antimicrobial absorbent material.

It is an aspect of this invention that thorough drying is accomplished by application of infrared heat, radiant heat, or hot air.

It is an aspect of the current inventive method that an additional step of rinsing, washing, or extracting will remove any leachable unbonded portion of said antimicrobial cationic polyelectrolyte from the inherently antimicrobial material.

It is an aspect of the current inventive method that said antimicrobial cationic polyelectrolytes are polymeric molecules containing at least three quaternary ammonium active units per molecule.

It is an aspect of the current inventive method that said antimicrobial cationic polyelectrolytes are polymeric molecules having an average degree of polymerization selected from the group consisting of 3 to 25,000, 20 to 10,000, and 100 to 2500.

It is an aspect of the current inventive method that said antimicrobial cationic polyelectrolytes are defined as polymeric molecules having a multiplicity (i.e. more than three) of cationic charges per polymeric molecule, or a net cationic charge excess of greater than three charges per polymeric molecule. "Net cationic charge excess" is defined as the sum of all the cationic charges in a given molecule minus the sum of all negative charges in the same molecule, not including the charges of any associated counterions (such as chloride ions) which are not covalently bonded to the polymeric molecule, and shall be considered to be a positive number equal to or greater than three, for the purposes of this invention.

Charge density is a measure of the relative amount of cationic charge in a given cationic polyelectrolyte, and higher antimicrobial efficacy will generally correlate with higher charge density for a given polymer. It is an aspect of this invention that the cationic polyelectrolytes have a minimum excess cationic charge of greater than approximately 1 mole (1 mole equals $6.02 \times 10^{23}$) per 25,000 grams of cationic polyelectrolyte (the weight of cationic polyelectrolyte includes the weight of the polymer component plus the weight of any associated counterions). Preferably, the cationic polyelectrolytes have a minimum excess cationic charge of greater than approximately 1 mole per 2,500 grams of cationic polyelectrolyte. More preferably, the cationic polyelectrolytes have a minimum excess cationic charge of greater than approximately 1 mole per 500 grams of cationic polyelectrolyte. Even more preferably, the cationic polyelectrolytes have a minimum excess cationic charge of greater than approximately 1 mole per 212 grams of cationic polyelectrolyte. Most preferably, the cationic polyelectrolytes have a minimum excess cationic charge of equal to greater than approximately 1 mole per 162 grams of cationic polyelectrolyte.

Zeta potential refers to the electrostatic potential generated by the accumulation of ions at the surface of a colloidal particle which is organized into an electrical double-layer consisting of the Stern layer and the diffuse layer of a material. Zeta potential and instruments used to measure zeta potential are well known in the art. The zeta potential of a successfully treated substrate should be significantly higher than that of an untreated substrate, due to the presence of the antimicrobial cationic polyelectrolyte. Thus, the antimicrobial efficacy of a treated substrate can be determined by measuring its zeta potential. It is an aspect of the current inventive method that the zeta potential of the inherently antimicrobial material produced is negative (less than zero).

It is an aspect of the current inventive method that said antimicrobial cationic polyelectrolytes are polymeric phosphonium compounds containing at least three quaternary phosphonium active units per molecule.

It is an aspect of the current inventive method that said antimicrobial cationic polyelectrolytes are comprised, in whole or in part, of monomeric units having the structure $CH_2=CR-(C=O)-X-(CH_2)_n-N^+R'R''R'''//Y^-$; wherein, R is hydrogen or methyl, n equals 2 or 3, X is either O, S, or NH, and R', R'' and R''' are independently selected from the group consisting of H, C1 to C16 alkyl, aryl, arylamine, alkaryl, and aralkyl, and $Y^-$ is an anionic counterion to the positive charge of the quaternary nitrogen; diallyldimethylammonium salts; vinyl pyridine and salts thereof; vinylbenzyltrimethylammonium salts; diallyldialkylammonium salts and vinylbenzyltrialkylammonium salts.

It is an aspect of the current inventive method that said antimicrobial cationic polyelectrolytes are comprised, in whole or in part, of monomeric units having the structure $CH_2=CR-(C=O)-X-(CH_2)_n-NR'R''$; wherein, R is hydrogen or methyl, n equals 2 or 3, X is either O, S, or NH, and R' and R'' are independently selected from the group consisting of H, C1 to C16 alkyl, aryl, arylamine, alkaryl, and aralkyl.

It is an aspect of the current inventive method that said antimicrobial cationic polyelectrolytes are polymeric molecules known as polyDADMAC comprised, in whole or in part, of diallyldimethylammonium chloride, (also known as DADMAC).

It is an aspect of this invention that said antimicrobial cationic polyelectrolytes are comprised of polyDADMAC homopolymer or polyVBTAC homopolymer, where "polyVBTAC" means poly(vinylbenzyltrimethylammonium chloride). "Homopolymer" is defined as a polymeric material consisting of multiple units derived from a single type of polymerizable monomer.

It is an aspect of the current inventive method that said antimicrobial cationic polyelectrolytes are polymeric molecules comprised, in whole or in part, of monomeric units selected from the group consisting of dimethylaminoethyl methacrylate, dimethylaminoethyl methacrylate (hydrogen chloride quaternary), dimethylaminoethyl methacrylate (methyl chloride quaternary) and dimethylaminoethyl methacrylate (benzyl chloride quaternary).

It is an aspect of the current inventive method that said antimicrobial cationic polyelectrolytes are comprised, in whole or in part, of monomeric units selected from the group consisting of dimethylaminoethyl acrylate, dimethylaminoethyl acrylate (hydrogen chloride quaternary), dimethylaminoethyl acrylate (methyl chloride quaternary) and dimethylaminoethyl acrylate (benzyl chloride quaternary).

It is an aspect of the current inventive method that said substrate is comprised, in whole or in part, of cellulose.

It is an aspect of the current inventive method that said substrate is comprised, in whole or in part, of at least one cellulosic material selected from the group consisting of hydroxyethyl cellulose, carboxymethyl cellulose, methyl cellulose, rayon, cotton, linen and wood pulp.

It is an aspect of the current inventive method that said inherently antimicrobial material has an absorbent capacity for aqueous fluids.

It is an aspect of the current inventive method that said inherently antimicrobially material has an absorbent capacity for aqueous biological fluids.

It is an aspect of the current inventive method that said substrate is a woven, flexible material.

It is an aspect of the current inventive method that said substrate is a non-woven, flexible material.

It is an aspect of the current inventive method that said substrate is wood or lumber.

It is an aspect of the current inventive method that said substrate is paper.

INDUSTRIAL APPLICABILITY

It is an aspect of the current inventive method that said inherently antimicrobial material comprises all or part of a wound dressing, a burn dressing, a sanitary pad, a tampon, an intrinsically antimicrobial absorbent dressing, a diaper, toilet paper, a sanitary wipe, a sponge, a cotton swab, a surgical gown, an isolation gown, a lab coat, a glove, surgical scrubs, a head cover, a hair cover, a face mask, a suture, a floor mat, a lamp handle cover, an exam table cover, a cast liner, a splint liner, padding, gauze, blood transfer tubing, a blood transfer storage container, sterile packaging, a mattress cover, bedding, a sheet, a towel, clothing, underwear, a sock, shoecover, an automobile air filter, an airplane air filter, an HVAC system air filter, a military protective garment, an apparatus for protection against a biohazard or biological warfare agent, lumber, food packaging material, meat packaging material, fish packaging material, apparel for food handling, a surface for food preparation, a contact lens, carpet, wood, lumber, paper, or paper currency.

Definitions

"Microbe" or "microorganism" refers to any organism or combination of organisms such as bacteria, viruses, protozoa, yeasts, fungi, molds, or spores formed by any of these.

"Antimicrobial" refers to the microbicidal or microbistatic properties of a compound, composition, article, or material that enables it to kill, destroy, inactivate, or neutralize a microorganism; or to prevent or reduce the growth, ability to survive, or propagation of a microorganism.

"Substrate" refers a surface or medium upon which an antimicrobial polyelectrolyte is chemically bonded.

"Cationic polyelectrolyte" means a polymer molecule with multiple cationic sites or moieties which are covalently bonded to the polymer, or attached to the molecular structure of the antimicrobial polymer by covalent chemical bonds, and are part of the polymer molecular structure, and that said cationic sites or moieties are located either in the main-chain of the polymer, or in side-groups of the polymer. "Main-chain" and "side-groups" are terms commonly used to describe polymer molecular structure and will be familiar to one skilled in the art.

The term "quaternary ammonium" is common chemical nomenclature and it meaning will be understood by one skilled in the art. There are two types of quaternary ammonium compounds: acidic, and non-acidic. Acidic quaternary ammonium compounds are acid salts of amines, and are characterized by having a N—H covalent bond wherein the N—H bond is reactive with bases. Non-acidic quaternary ammonium compounds do not have this N—H bond, and are not reactive with bases. Non-acidic quaternary ammonium compounds are preferred in the practice of this invention.

By "inherently antimicrobial" is meant a property of a material wherein said material would exhibit antimicrobial activity or properties in the absence of any antimicrobial activity or properties contributed by agents, compounds, or additives which are not integral to the material, not chemically bonded to the material, or detachable from the material, or after the removal or depletion of such agents, compounds, or additives from the material. "Inherently antimicrobial" does not mean that the material contains no leachable agents with antimicrobial activity.

By "non-leaching" is meant that the antimicrobial cationic polyelectrolytes of the present invention, once attached to the material or substrate via the method of the current invention, do not appreciably separate from, migrate out of, or away from the material or substrate, enter a wound, or otherwise become non-integral with the material or substrate under standard uses. By "not appreciably separate" is meant that no more than an insubstantial amount of antimicrobial cationic polyelectrolyte separates, for example less than one percent, preferably less than 0.1 percent, more preferably less than 0.01 percent, and even more preferably less than 0.001 percent of the total quantity of antimicrobial cationic polyelectrolyte. Alternatively, "not appreciably separate" means that the solution concentration of antimicrobial cationic polyelectrolyte resulting from separation of attached antimicrobial cationic polyelectrolyte, in a liquid in contact with the material or substrate, does not exceed a predetermined level, for example less than 0.01%, preferably less than 0.005%, and more preferably less than 0.001%. Alternately, depending on the application, "not appreciably separate" may mean that no adverse effect on wound healing or the health of an adjacent tissue of interest is measurable. It should be understood that particular definition may depend on the application in which the invention is used. For instance, in textile applications, the desire is to maintain efficacy over a prolonged period of use, thus only a very gradual loss of antimicrobial material over an extended time would be acceptable, regardless of the amount leached at any given point in time. For medical applications such as wound dressings, the overriding concern would be to ensure that the localized concentration of leachable material remains below a specific level at a given point in time, or leads to no adverse effects over the period of use.

In regard to the foregoing definition, it is noted that "non-leachable" refers to the bond between the polymer chain and the substrate. In certain embodiments of the present invention, a bond between the polymer backbone and one or more type of antimicrobial group may be intentionally made to be more susceptible to release, and therefore more leachable. This may provide a benefit where it is desirable for a percentage of the antimicrobial groups to be selectively released under certain conditions. However, it is noted that the typical bond between the polymer chain and antimicrobial groups envisioned and enabled herein are covalent bonds that do not leach under standard exposure conditions.

By "degree of polymerization" is meant the number of monomers that are joined in a single polymer chain. For example, in a preferred embodiment of the invention, the average degree of polymerization is in the range of about 5 to 1,000. In another embodiment, the preferred average degree of polymerization is in the range of about 10 to 500, and in yet another embodiment, the preferred average degree of polymerization is in the range of about 10 to 100.

"Self-crosslinking" means that the polymer has the capability to undergo a chemical or physical reaction with itself which results in bridging, bonding, or attachment between its individual polymer chain molecules to form a three dimensional network structure consisting essentially of a single large molecule, without the need to react with any outside reagents such as catalysts or crosslinking agents which are not already part of the polymer's molecular structure.

A "cellulosic material" means a natural material made in whole or in part of cellulose or a synthetic material derived from cellulose or having chemical and physical properties similar to cellulose.

DETAILED DESCRIPTION

The current invention provides a method of manufacture of an inherently antimicrobial material that establishes a non-leaching attachment of antimicrobial cationic polyelectrolytes onto a substrate. The non-leaching attachment of antimicrobial cationic polyelectrolytes to a substrate that has been exposed to a solution of antimicrobial cationic polyelectrolytes (the treatment solution) occurs during the thorough drying of the substrate. In one exemplary embodiment of the inventive method, a substrate containing cotton, or a cellulose derivative, is thoroughly dried after it has been exposed to an aqueous solution of polymeric diallyldimethylammonium chloride (i.e. polyDADMAC) having an average degree of polymerization of ranging from 5 to 10,000, or more preferably 30 to 5,000, and most preferably 100 to 2500.

As used herein, "antimicrobial" refers to the property of a compound, composition, article, or material that enables it to destroy, neutralize or kill a microorganism. As used herein, "microbe" or "microorganism" refers to any organism or combination of organisms able to cause infection, such as bacteria, viruses, protozoa, yeasts, fungi, or molds.

It is an aspect of the inventive method that the antimicrobial cationic polyelectrolytes comprise polymeric phosphonium compounds. Polymeric phosphonium compounds are known to possess antimicrobial properties. Several reports in the chemical literature concern the synthesis of various antimicrobial synthetic polymers. For example, the synthesis of polymeric phosphonium derivatives of styrene has been reported by Endo, T., et al in "*Novel Polycationic Biocides: Synthesis and Antibacterial Activity of Polymeric Phosphonium Salts*" (Journal of Polymer Science Part A: Polymer Chemistry, 31, pp. 335-342, 1993). Phosphonium quaternary polymers have been shown to be up to 4 orders of magnitude more effective as antimicrobial agents than the corresponding nitrogen quaternary polymers.

It is an aspect of the inventive method that suitable concentrations of the antimicrobial cationic polyelectrolytes in the treatment solution range from about 20 wt % to about 0.01 wt %, and preferably between 10 wt % and 0.1 wt %. The actual concentration chosen for a particular application depends on, among other things, the molecular weight of the particular antimicrobial cationic polyelectrolytes and the resultant viscosity of the solution. At a minimum, a sufficient amount of antimicrobial must be incorporated into the product in order to provide the desired degree of antimicrobial activity (as described below). There is no distinct upper limit to the concentration of the solution of the antimicrobial cationic polyelectrolytes that can be used, other than practical constraints, such as viscosity, solubility, and cost, which will vary according to the antimicrobial cationic polyelectrolyte utilized.

It is an aspect of the inventive method that there is no minimum incubation time after the loading of substrate with antimicrobial by exposure of substrate to a solution of antimicrobial cationic polyelectrolytes. The loading of substrate with antimicrobial cationic polyelectrolytes is complete as soon as the substrate is wetted with antimicrobial cationic polyelectrolyte solution. Uniformity of wetting allows the final product to have an even and uniform distribution of attached antimicrobial cationic polyelectrolytes, but is not a necessary prerequisite for attachment of antimicrobial cationic polyelectrolytes to any specific area of the substrate.

To establish a non-leaching attachment of antimicrobial cationic polyelectrolytes to a substrate, the substrate which has been loaded with antimicrobial cationic polyelectrolyte solution must be then thoroughly dried. Thorough drying is necessary to impart the non-leaching property conveyed by the inventive method to at least a portion of the antimicrobial cationic polyelectrolytes that were in the solution contacting the substrate. It is an aspect of the inventive method to use any temperature and time combination that results in thorough drying of said material. As used herein, thoroughly dried means, for instance, that a substrate exposed to a solution of antimicrobial cationic polyelectrolytes is then dried to a constant weight. As used herein, dried to a constant weight means dried to the point at which continued application of the chosen drying procedure will no longer result in a considerable additional measurable loss of weight due to evaporation of water or other solvent. Attainment of constant weight is a useful tool to measure extent of dryness; however, the attainment of constant weight is not the actual factor that enables non-leachable attachment of the antimicrobial to the substrate. That attachment is produced by the drying process itself (removal of water from the system). The particular temperatures and drying times necessary to achieve thorough drying depend, among other things, on the particular substrate material, the initial amount of moisture in the article, the weight and size of the article, the amount of airflow provided to the article during drying, and the humidity of the air or other medium contacting the article. Illustrative examples are provided below which describe the effect of achieving various degrees of dryness by allowing the treated substrate to reach moisture equilibrium at specific points of relative humidity. Any drying apparatus, drying method, and temperature and drying time combination that thoroughly dries the treated substrate and imparts a non-leachable bond between the substrate and antimicrobial is sufficient. For purposes of illustration, depending on the particular characteristics of a particular application, the drying step may be performed in an oven (e.g. 80° C. for 2 hours), in a high throughput furnace (e.g. 140° C. for 30 seconds), in a clothes dryer, in a desiccator, in a vacuum chamber, in a dehumidifier, in a dehydrator, or in a lyophilizer (freeze dryer). Infrared heat, radiant heat, microwave, and hot air are all suitable drying methods for the substrate which has been exposed to a solution of antimicrobial cationic polyelectrolytes. The upper limit of drying temperature for a particular application will generally be determined by the degradation temperature of the particular substrate or antimicrobial cationic polyelectrolyte being treated.

Unconventional or nontraditional drying methods may be utilized. For instance, simply freezing of the wet substrate which has been treated with antimicrobial solution has been found to impart a non-leaching bonding of the antimicrobial to the substrate. Presumably, this is due to the fact that upon freezing the dissolved antimicrobial is pushed out from the crystallizing ice structure, leaving the previously dissolved antimicrobial deposited onto the surface of the substrate, and forming a non-leaching bond between the substrate and antimicrobial cationic polyelectrolytes. This results in the same overall effect as conventional drying, wherein the water is separated from the polymer by evaporation. As expected, rapid freezing, such quenching the wet material in liquid nitrogen, is not as effective at promoting nonleachable attachment because of insufficient time for to achieve separation of antimicrobial from water.

A similar effect is observed when the substrate which has been treated with an aqueous solution of antimicrobial is subsequently washed with an organic solvent that is miscible with water, in order to remove water, followed then by washing in water. The conventional drying step may be omitted; however, non-leachable bonding of the antimicrobial to the substrate may still be achieved because the solvent removes water in a manner similar to what happens during normal drying. Generally, a water soluble polymer such as polyDADMAC will be insoluble or less soluble in an organic solvent, compared to water, and the bonding effect will be more pronounced as the solubility of the antimicrobial polymer in the chosen solvent is lower. For instance, it has been found that t-butyl alcohol and tetrahydrofuran promote non-leachable bonding of antimicrobial polymer to a cotton substrate better than dimethyformamide or methanol.

It is an aspect of this invention that the antimicrobial polymer is applied to the substrate as an aqueous solution, and that organic solvents are not required. The use of aqueous solutions is an advantage over the use of organic solvents because of various issues including cost, safety, health, and regulatory. It is also possible to utilize mixed solvents, such as water/alcohol mixtures, for initial application of the antimicrobial to the substrate using the described process, combined with any of the drying methods described above. This will depend on the solubility of the antimicrobial in the mixed solvent systems. For instance, mixtures of alcohol and water may be used. It may also be possible to use completely non aqueous solvent systems; however, it is necessary that the antimicrobial be soluble in the chosen solvent system.

Other drying methods such as supercritical fluid drying may also be successfully employed in the practice of this invention. Freeze drying may be used; however, is unnecessary since merely freezing of the substrate which has been wetted with antimicrobial is sufficient. Subsequent sublimation or removal of the ice phase is not necessarily required in order to effect a non-leachable bond between the substrate and the antimicrobial cationic polyelectrolytes.

It is an aspect of the inventive method that prior to the drying step, in order to lessen the time needed to thoroughly dry the loaded substrate, and/or to reduce consumption of materials, a mechanical action or force may be applied to the loaded substrate to remove excess antimicrobial-containing solution from the loaded substrate. Any mechanical action or force may be applied; however, it is preferred that such action or force be uniform in order to provide an even distribution of remaining solution within the loaded substrate as the solution is forced out. Examples of such mechanical action or force include, but are not limited to, rolling, pressing, squeezing, centrifugation, and the like. It should be noted application of a mechanical force to remove excess solution prior to drying is distinct from the drying procedure in that the mechanical force removes both the antimicrobial and the carrier solution, while the drying procedure removes only the carrier solution, through evaporation, but leaves the antimicrobial in the loaded substrate.

The non-leaching attachment of antimicrobial cationic polyelectrolytes produced by said inventive method has been demonstrated by boiling the treated articles of this invention in water containing a range of salt concentrations, and in water having a range or various neutral, acidic, and alkaline pH values, followed by verification that the treated articles retain antimicrobial activity. In addition, antimicrobial efficacy of the materials having non-leaching attachment of the antimicrobial cationic polyelectrolyte has been demonstrated after exposure of the inherently antimicrobial materials to proteinaceous material in the form of fetal bovine serum.

It is an aspect of the current inventive method that a rinsing step may be optionally exercised. It is likely that when utilizing the method of the current invention, that only a portion of the total antimicrobial cationic polyelectrolytes applied to the substrate will actually become non-leachably bonded to the substrate; hence, the inherently antimicrobial material is likely to also contain some leachable antimicrobial cationic polyelectrolytes. The decision of whether or not to rinse the treated material will depend on whether a leaching antimicrobial property, in addition to the inherently non-leaching antimicrobial property, is desired in the final product. For some applications (e.g. textile applications), it may be desirable to retain some or all of the leachable portion of antimicrobial cationic polyelectrolytes in the final product, in combination with the non-leaching portion, because the leachable portion can contribute to the overall antimicrobial activity, at least initially, before the leachable portion becomes depleted. So, for example, where a particular application calls for retention of the leachable portion, it is suitable to utilize the inherently antimicrobial material after it has been thoroughly dried (without rinsing). For other applications (e.g. some wound dressings), it may be desirable to remove the leachable portion and retain only the non-leaching portion. For example, where a particular application calls for removal of the leaching portion, the thoroughly dried treated material can be repeatedly rinsed in fluid to remove the leachable portion of antimicrobial cationic polyelectrolytes that did not attach to the substrate during the thorough drying step. In one exemplary embodiment, the rinsing step can be considered complete when conductivity readings of the rinsate equal that of the input rinse fluid, indicating that the rinsate is free of unbounds. In another exemplary embodiment, the rinsing can be accomplished by using a salt solution, followed by rinsing in fresh water to remove both the leachable antimicrobial and salt in order to obtain the lowest possible level of leachable antimicrobial.

It is an aspect of the current inventive method that it can establish a non-leaching attachment of antimicrobial cationic polyelectrolytes to a variety of substrates. Natural and synthetic substrate materials amenable to the current inventive method include, but are not limited to, cellulose, cellulose derivatives, hydroxyethyl cellulose, carboxymethyl cellulose, methyl cellulose, rayon, cotton, wood pulp, linen, polysaccharide, protein, wool, collagen, gelatin, chitin, chitosan, alginate, starch, silk, polyolefin, polyamide, fluoropolymer, polyvinyl chloride (PVC), vinyl, rubber, polylactide, polyglycolide, acrylic, polystyrene, polyethylene, polypropylene, nylon, polyester, polyurethane, and silicone, all of which may be verified by routine experimentation based on the present disclosure.

It is an aspect of the current inventive method that the antimicrobial activity exhibited by materials manufactured by the method is very robust. In contrast, some competing formulations, such as those marketed by AEGIS Environments, have been found to be inactivated after exposure to blood (see EP 0136900) or 10% fetal bovine serum. In one exemplary embodiment of the current inventive method, the antimicrobial activity of non-leachably attached polymeric molecules of the quaternary ammonium compound diallyldimethylammonium chloride remains robust in the presence of 10% fetal bovine serum, as described in the examples below. This aspect of the current inventive method will permit antimicrobial activity to persist in the presence of bodily fluids, which is a valuable and useful property for many applications in the health industry.

It is an aspect of this invention that silane, silicone, or siloxane antimicrobial cationic polyelectrolytes are not applied to the substrate or incorporated into the antimicrobial material, as silane, silicone or siloxane compounds generally will impart a water-repellent character to a substrate of composition, thus reducing the absorbency of the material.

It is an aspect of this invention that the process does not require the use of an inert atmosphere, vacuum, high pressure, irradiation, organic solvents, catalysts, excessively high temperatures, and/or volatile, expensive, flammable, or toxic reagents to produce the antimicrobial material. This is in contrast to prior methods which require such measures in order to produce a cellulosic substrate with attached quaternary ammonium.

It is an aspect of specific embodiments of the current inventive method that the attachment of antimicrobial cationic polyelectrolytes to a fabric substrate has a softening effect on fabric, and can thereby reduce the amount of softener that must to be applied to the fabric.

It is an aspect of the specific embodiments of the current inventive method that cationic fabric softening agents can be added to said treatment solution to impart an enhanced antimicrobial effect to the product of said inventive method. We have determined that cationic softening agents alone do not show any permanent antimicrobial effect, and therefore we regard this observation of the synergic interaction between the cationic softening agents and the cationic antimicrobial cationic polyelectrolyte to be a novel and enhancing effect.

Some substrates are more amenable to treatment by selected antimicrobial cationic polyelectrolytes than other similar substrates. For instance, rayon and cotton are both forms of cellulose; however, it has been found (unexpectedly) that cotton treated using polyDADMAC in accordance with the methods described herein gives a product with a significantly higher antimicrobial power than rayon treated in an identical manner. This is an unexpected result, and it has been found to be particularly useful, for instance, in the manufacture of an antimicrobial wound dressing. Wood pulp is also significantly more reactive than rayon when used in conjunction with polyDADMAC. These differences may not exist, or even be reversed when different antimicrobial cationic polyelectrolytes are employed.

The strong non-leachable binding of the antimicrobial cationic polyelectrolytes to the substrates, as described herein, is unexpected based on comparisons to other model systems such as formation of polyelectrolyte complexes between cationic polymers and clay or mica particles. For instance, treatment of mica with an aqueous solution of polyDADMAC, followed by drying and washing in distilled water results in a material capable of binding an anionic dye, as described in the following examples; however, if this treated material is subsequently rinsed in saline solution, the ability to bind anionic dye is substantially diminished, or completely lost, indicating a loss of polyDADMAC from the material. As such, the clay-PolyDADMAC system does not constitute an antimicrobial bonded to a substrate in a non-leachable manner. Thus, the mechanism of binding of the cationic antimicrobial to the surface as described for the current invention, is presumably not strictly an ion-exchange type of process, as exhibited by the polyDADMAC-mica system. Although it is known that cellulose normally exhibits a net negative surface charge (or zeta potential), it is not considered to be an ionic material. Thus, ionic interactions between cellulose and a cationic species would not be expected to be exceptionally strong or irreversible. Presumably, the strong interactions which result in non-leachable bonding observed between cotton and polyDADMAC, for example, are based on a balanced combination of hydrophobic and ionic interactions. These interactions are formed during drying or removal of water from the system. The overall strength of these interactions is compounded by the polymeric nature of the substrate and the antimicrobial cationic polyelectrolyte, which results in a multiplicity of binding effects. This multiplicity of binding effects means that each polymeric antimicrobial molecule is held to the substrate through bonding attractions emanating from many different points along the molecular structure, which combine to give a very strong overall bond between the substrate and the polymeric antimicrobial cationic polyelectrolyte. This multiplicity of binding effects cannot be achieved for smaller molecules, such as monoquats (benzalkonium chloride, or DDDAMC, for instance). It cannot be ruled-out that the drying process induces the formation of covalent chemical bonds between the substrate and the antimicrobial cationic polyelectrolyte. This could occur, for instance, by condensation (dehydration) reactions of the hydroxyl groups on cellulose with reactive sites on the antimicrobial molecules. Insertion of portions of the antimicrobial cationic polyelectrolytes into the crystalline structure of the cellulose substrate could also be partially responsible for the observed binding. Polymeric quaternary ammonium compounds exhibit the non-leaching attachment described herein. The use of non-polymeric quaternary ammonium compounds according to the method of this invention does not produce a nonleachable attachment. Comparative examples of the lack of non-leachable attachment of nonpolymeric quats are given below. In light of the behavior of the nonpolymeric quats, it would not be obvious to one skilled in the art that polymeric quats would become non-leachably attached when used in the method of the current invention.

The discovery that drying of a cellulose substrate to which a cationic polyelectrolyte has been applied causes irreversible, non-leachable bonding between at least a portion of the applied cationic polyelectrolyte has not previously been described. Onabe ("*Studies of Interfacial Properties of Polyelectrolyte-Cellulose Systems. I. Formation and Structure of Adsorbed layers of Catioinic Polyelectrolyte-(Poly-DMDAAC) on Cellulose Fibers*" Journal of Applied Polymer Science. Vol. 22, 3495-3510 (1978)) studied the adsorption of polyDADMAC onto cellulose fibers. The cellulose fibers were soaked in polyDADMAC solutions for 24 hours, and then rinsed to remove excess polyDADMAC prior to analysis. Based on the studies and data presented herein to describe the current invention, it will be recognized that such a rinsing step (without first drying the exposed substrate) does not produce an inherently antimicrobial material with cationic polyelectrolyte non-leachably attached to the cellulose substrate. Apparently, the rinsing procedure described by Onabe is not sufficient to remove all of the applied cationic polyelectrolyte; however, the amount remaining is insufficient to provide antimicrobial efficacy. This has been verified, as described in the examples below. Onabe does not discuss antimicrobial properties of cellulose materials with adsorbed cationic polyelectrolytes, nor does the reference discuss whether those materials show any non-leachable bonding. Onabe attributes absorption of cationic polyelectrolyte to cellulose as strictly an electrostatic interaction, which is inconsistent with the observations of the non-leachable properties of the current invention when exposed to saline solutions.

It is known; however, that enhanced antimicrobial properties are exhibited by polymeric quaternary compounds, relative to monomeric quats (keda, T., "*Antibacterial Activity of Polycationic Biocides*", Chapter 42, page 743 in: *High Performance Biomaterials*, M. Szycher, ed., Technomic, Lancaster, Pa. (1991); and Ikeda T, Yamaguchi H, and Tazuke, S "*New Polymeric Biocides: Synthesis and Antibacterial Activities of Polycations with Pendant Biguanide Groups*"; *Antimicrob. Agents Chemother.* 26(2), p139-44 (1984)).

The unexpected nature of the observation that nonleachable binding is caused by employment of a drying step is further evidenced by the fact that while it is generally known that a strong polyelectrolyte complex (PEC) can be formed between oppositely charged polymers, formation of such PECs generally proceeds spontaneously, even in aqueous solution. For instance, aqueous solutions of oppositely charged polyelectrolytes may be mixed, resulting in immediate precipitation of a solid PEC. For instance, in U.S. Pat. No. 6,776,985, Saller reports the formation of PEC microcapsules formed by reaction of aqueous solutions of cellulose sulphate and polyDADMAC. These solid PEC materials are formed within milliseconds upon mixing of the two aqueous solutions, without the need for drying or removal of water. It should be noted that cellulose sulphate is substantially different substance than the substrate materials of the current invention (such as cotton), in that cellulose sulphate is a highly ionic substance which is soluble in water.

The inherently antimicrobial materials produced using the current inventive method are distinct from those described by Senka (JP 09078785, see above discussion), in that the inherently antimicrobial materials produced by the current invention are produced due to specific interactions on the molecular level between the substrate and the applied polymeric antimicrobial cationic polyelectrolyte, as described above. In contrast, the materials described by Senka depend on the interaction of individual copolymer molecules with each other to form a solid insoluble network. In other words, the copolymers described by Senka are capable of undergoing self-crosslinking. The term "self-crosslinking" means that the polymer has the capability to undergo a chemical or physical reaction with itself which results in bridging, bonding, or attachment between its individual polymer chain molecules to form a three dimensional network structure consisting essentially of a single large molecule, without the need to react with any outside reagents such as catalysts or crosslinking agents which are not already part of the polymer's molecular structure. The polymer molecules are individually bonded to the substrate, and hence behave as part of the substrate. Once crosslinked, the polymer becomes insoluble; although, the crosslinked polymeric network may be capable of absorbing water to form a gel. The antimicrobial cationic polyelectrolytes of the current invention are not self-crosslinking. Since there is no crosslinked polymer network to become attached to the surface of the inherently antimicrobial materials of the current invention, the materials retain the general physical properties of the untreated substrates such as appearance, feel, texture, hand, softness, and flexibility. Crosslinked coating materials could also tend to cement individual fibers together, or fill-in voids and pores, both of which could adversely affect substrate properties. In contrast the materials prepared using a coating, such as described by Senka, may be expected to become stiff, brittle, or non-adherent due to intermolecular association or crosslinking of the self-crosslinking polymeric antimicrobials used. As an analogy of the differences between the two types of systems, consider the differences between a varnish used to finish wood by providing a protective glossy coating, versus a wood-stain type of product which merely colors the wood itself without changing its texture. Varnish materials are similar to the materials of Senka, in that they are generally self-crosslinking, and once they dry they become insoluble. The dried varnish; however, may be easily peeled away from the underlying wood surface. The wood-stain, on the other hand, will generally be more substantive to the wood substrate and more difficult to remove. The interactions of the wood-stain are only between the individual stain molecules and the wood substrate. The stain molecules are more similar to the antimicrobial cationic polyelectrolytes of the current invention in that they do not interact with themselves to form a three dimensional coating.

It should be emphasized that in most processes intended to produce a final material that is free from leachable additives, it is generally not intuitive to dry the product before rinsing out any "extra" non-bonded additive. Usually, it will be more cost effective to rinse or wash the material prior to final drying in order to avoid the need for drying more than once. Many treatment methods (antimicrobial and otherwise) rely on a reaction between the substrate and the applied additive, and this reaction usually takes place in solution. Examples of this are seen in many of the references cited above (see for instance: Payne, Onabe, Lee, Abel, and Batich). This rinsing step prior to drying of the treated material is also widely used in textile treatment processes such as dye treatment using disperse, reactive, or vat dyes. In the case of the current invention; however, the reaction between the substrate and antimicrobial additive is actually caused to occur by the drying step. Hence, rinsing or washing cannot be done until after the material has been dried, or else the additive would be completely removed.

Antimicrobial efficacy may be measured by appropriate methods which will be familiar to one skilled in the art. In particular, a modified version of the American Association of Textile Chemists and Colorists (AATCC) Test Method 100 ("*Antibacterial Finishes on Textiles: Assessment of*"), a test designed to test antibacterial finishes of textile materials is useful, and is described in the following examples. One skilled in the art will recognize that a significant reduction in the number of viable bacteria should be observed when the antimicrobial material is tested according to this method, which utilizes a non-antimicrobial (untreated) material with similar physical properties as a "negative control". Preferably, the reduction in bacterial levels (vs. negative control) should be a factor of 1000 (a "3-log kill", or 99.9% reduction). More preferably, the reduction in bacterial levels (vs. negative control) should be a factor of 10,000 (a "4-log kill", or a 99.99% reduction). Even more preferably, the reduction in bacterial levels (vs. negative control) should be a factor of 100,000 (a "5-log kill", or a 99.999% reduction). Most preferably, the reduction in bacterial levels (vs. negative control) should be a factor of 1,000,000 (a "6-log kill", or 99.9999% reduction). It should be noted that limitations of the test method may result in lower numerical reductions of bacterial levels if the number of viable bacteria in the negative control is low. For instance, if the negative control contains only 500 viable bacteria (colony forming units), a reduction factor of 500 (a 2.7-log kill) is the maximum possible result; however, in this case the result represents a 100% reduction of bacterial population, and is perfectly acceptable. Generally, when the standard method is followed using absorbent textile test articles, the growth of most commonly-encountered bacteria in the negative control will be in the range of 100,000 to 10,000,000 colony forming units.

Quaternary ammonium compounds, including the non-leachably bound antimicrobials of this invention, generally show greater activity against Gram+ bacterial organisms than against Gram− bacterial organisms. Thus, a higher level of bonded antimicrobial is needed in order to achieve the same antimicrobial efficacy against Gram− organisms. Surprisingly, it is found that the necessary levels of non-leachably bound antimicrobial in materials prepared by the current invention are substantially lower than those required when other methods are used to attach similar antimicrobials to similar substrates. For instance, in a specific embodiment of this invention, a cotton substrate treated with a 2% aqueous solution of polyDADMAC, followed by drying and sequential rinsing in saline and deionized water was found to have greater than 6-log efficacy against a wide range of both Gram+ and Gram− organisms (see examples below for experimental details). Elemental analysis for nitrogen content revealed that the overall content of quaternary ammonium antimicrobial cationic polyelectrolyte (polyDADMAC) was less than 1 weight percent (<1 wt %). In contrast, materials produced using antimicrobial treatments involving graft copolymerization of polyDADMAC monomer onto cotton substrates using the methods described by Batich, U.S. Pat. No. 7,045,673 and application US 20020177828 A1, must contain greater than approximately 5 wt % antimicrobial for equivalent antimicrobial efficacy when the same substrate (cotton), and the same cationic polyelectrolyte antimicrobial cationic polyelectrolyte (polyDADMAC) is used. A comparative example showing the antimicrobial efficacy of inherently antimicrobial materials made utilizing the grafting method of Batich is provided below.

Preferably, the antimicrobial composition of the current invention is effective against Gram+ bacteria. More preferably, the antimicrobial of the current composition is effective against Gram+ bacteria, and Gram− bacteria. Most preferably, the antimicrobial of the current composition is effective against Gram+ bacteria, Gram− bacteria, and also fungal and viral organisms.

When a quaternary ammonium compound is utilized as the antimicrobial agent in the practice of this invention, it is possible to estimate the relative degree of binding of quaternary antimicrobial to the substrate by utilizing a dye test which is described in the examples given below. It is found that there is a positive correlation between the results of the dye test described, and the antimicrobial performance. Generally, materials which exhibit a dark blue color result using the specified test procedure, will exhibit excellent antimicrobial activity (>6-log reduction of *pseudomonas*, for instance), while lighter blue intensity results correlate to lower antimicrobial efficacy.

In light of the general disclosure provided herein above, with respect to the manner of practicing this inventive method, those skilled in the art will appreciate that this disclosure enables the practice of the inventive method as defined in the attached claims. However, the following experimental details are provided to ensure a complete written description of this invention, including the best mode thereof. However, it will be appreciated that the scope of this invention should not be construed in terms of the specific examples provided. Rather, the scope of this invention is to be apprehended with reference to the claims appended hereto, in light of the complete description of this inventive method constituted by this entire disclosure.

EXAMPLE 1A

Treatment of a Rayon Substrate with Polymerized Diallyldimethylammonium chloride—Leachable Portion Rinsed.

This example demonstrates the binding of a polymeric quaternary compound to a substrate. A nonwoven rayon gauze substrate was submerged in a 5% aqueous solution of polymerized diallyldimethylammonium chloride. After the substrate was saturated with the polymer solution, the substrate was pressed free of excess solution by rolling. The wetted and pressed rayon substrate was then placed into 50° C. drying oven for four hours, until the treated rayon substrate was dried thoroughly. To remove any polymer that did not become non-leachably attached to the treated rayon substrate during the drying step, the treated rayon substrate was rinsed repeatedly with water until conductivity readings of the rinsate equaled that of the input rinse water, indicating that the rinsate was free of unbound polymer. To verify the attachment of cationic polymer, the zeta potential and dye binding behavior were measured, as described in Example 5, below.

EXAMPLE 1B

Treatment of a Rayon Substrate with Polymerized Diallyldimethylammonium Chloride (Comparative Example to Demonstrate Effect of Drying Step Being Omitted).

The method of Example 1A was followed, except that the drying step was omitted. This results in no significant attachment of the antimicrobial to the substrate.

EXAMPLE 2

Treatment of a Rayon Substrate with Polymerized Diallyldimethylammonium Chloride—Leachable Portion Retained.

This example demonstrates the binding of a polymeric quaternary compound to a substrate. A rayon substrate was submerged in a 5% aqueous solution of polymerized diallyldimethylammonium chloride. After the substrate was saturated with the polymer solution, the substrate was pressed free of excess solution by rolling. The wetted and pressed rayon substrate was then placed into 50° C. drying oven for four hours, until the treated rayon substrate was dried thoroughly.

EXAMPLE 3A

Treatment of a Cotton Material Suitable for Textile Applications with Polymerized Diallyldimethylammonium Chloride—Laboratory Scale Production.

This example demonstrates the binding of a polymeric quaternary compound to a substrate. A knitted cotton fabric substrate was submerged in a 5% aqueous solution of polymerized diallyldimethylammonium chloride. After the substrate was saturated with the polymer solution, the substrate was pressed free of excess solution by rolling. The wetted and pressed cotton substrate was then placed into 50° C. drying oven for four hours, until the treated cotton substrate was dried thoroughly.

EXAMPLE 3B

Treatment of a Cotton Material Suitable for Textile Applications with Polymerized Diallyldimethylammonium Chloride—Laboratory Scale Production—Soluble Portion Removed.

The method of Example 3A was followed. After thorough drying of the treated cotton substrate, it was washed twice in a large excess of 1% aqueous NaCl solution to remove any polymer that did not become non-leachably attached to the treated rayon substrate during the drying step. It was then rinsed repeatedly with water until conductivity readings of the rinsate equaled that of the input rinse water, indicating that the rinsate was free of unbound polymer.

EXAMPLE 3C

Treatment of a Cotton Material Suitable for Textile Applications with Polymerized Diallyldimethylammonium Chloride—Laboratory Scale Production—Soluble Portion Removed (Comparative Example Demonstrate the Effect of Drying Step Being Omitted).

The method of Example 3B was followed, except that the drying step was omitted. This results in no significant attachment of the antimicrobial to the substrate.

EXAMPLE 4

Treatment of a Cotton Material Suitable for Textile Applications with Polymerized Diallyldimethylammonium Chloride—Plant Scale Production.

Treated knitted cotton fabric substrate was prepared in an industrial setting using equipment typically found in the dye house of a textile mill where dyed or bleached cotton fabric emerges from the dye tumbler wet and is then transferred to a pad machine. In this example, the wet fabric direct from the dye tumbler was passed through the pad machine. The wet fabric then entered the pad bath by passing through extraction rollers, which were set to 350 psi and caused the fabric to lose some, if any, of the water it contained. Within the pad bath the fabric was immersed in a 5% aqueous solution of polymerized diallyldimethylammonium chloride. The treated fabric then exited the pad bath and passed through nip rollers, which were set to 150 psi. The treated fabric was then transited to a three-stage propane dryer with each stage set to 280° F. and with a transit time for the fabric of 60 seconds, which dried the treated fabric thoroughly. To remove any polymer that did not become non-leachably attached, the treated fabric substrate was rinsed using a dye tumbler with repeated fill and rinse cycles with water heated to 60° C., until the measured conductivity of the rinsate equaled that of the input rinse water.

EXAMPLE 5

Verification of Attachment of an Antimicrobial Polyelectrolyte to the Substrate using a BTB Dye Assay.

The pH indicator dye bromothymol blue (BTB) was used to test for the successful attachment of an antimicrobial polyelectrolyte to a substrate. This dye assay is best suited for use on substrates that have a neutral or negative zeta potential prior to treatment, such as cotton, rayon, and alginates because binding of the dye to the negatively charged (untreated) substrates is essentially zero; whereas the negatively charged dye molecule binds strongly to positively charged surfaces, such as those containing bonded non-leachable antimicrobial quaternary ammonium compounds. This method was used to test samples typical of those produced using the methods described in Examples 1A, 1B, 3B and 3C. Each sample was placed into a separate beaker and saturated with 0.5 wt % BTB dye solution that had been adjusted to pH>10 with ammonia. The samples were then rinsed repeatedly with water, until the rinsate no longer visibly contained any BTB dye. After the final rinse, the materials produced in Examples 1A and 3B (with drying step) were substantially blue in appearance, indicating the successful non-leachable attachment of the antimicrobial polyelectrolyte, while the samples produced in Examples 1B and 3C (no drying step) did not show any blue coloration, indicating the lack of any bonded antimicrobial quaternary material. It should be noted that the blue color of the material of Example 3B was significantly darker than that of Example 1A. This is an indication that a higher degree of bonding of antimicrobial quaternary compound is achieved when a cotton substrate is used as opposed to a rayon substrate, when the antimicrobial cationic polyelectrolyte employed is polymerized diallyldimethylammonium chloride. Note that depending on the pH of the rinse water, the dye color may appear either blue or greenish-yellowish. Adding a few drops of ammonia to the rinse water will convert the dye color to the blue form. In the practice of this invention, it is useful to evaluate the relative intensity of the final blue color (if any) according to the following scale: Not Blue, Very Light Blue, Light Blue, Blue, Dark Blue, Very Dark Blue. Although this is only a qualitative scale, the results can be quantified to some extent by comparison to standard samples, or by using standard methods of measuring color intensity that would be known to one skilled in the art. In general, it is found that the antimicrobial efficacy correlates to the intensity of the blue color, with samples showing only Very Light or Light Blue color having only low antimicrobial efficacy.

EXAMPLE 6

Verification of Attachment of the Cationic Compound to the Substrate Using a Zeta Potential Measurement, and Correlation of Zeta Potential and Antimicrobial Efficacy to Concentration of Antimicrobial Polymer Used in Treatment Solution.

Zeta potential is a measure of the surface charge of a material. The zeta potential of a successfully treated substrate should be significantly higher than that of an untreated substrate, due to the presence of the antimicrobial cationic polyelectrolyte. The zeta potential of each sample was determined by measuring the streaming potential of the fabric using a Brookhaven-Paar Physica EKA Electrokinetic Analyzer. Each sample was loaded individually into the cylindrical cell attachment forming a fiber plug in the cell. The distance between the Ag/AgCl electrodes was adjusted to 30 mm. Buffered millimolar potassium chloride was used as the streaming fluid. Eight measurements of the streaming potential were made for each sample. The reported zeta potential is an average of those calculated using each measured streaming potential value. To determine whether surface conduction had an effect on the measured streaming potential, the streaming fluid was then replaced with buffered 0.1M KCl and the zeta potential with surface conduction correction was determined. An untreated control sample was included for comparison. Approximately 2.5 to 3.0 g of treated or untreated rayon substrate material was compacted into the measurement cell and the electrodes were set to a specified separation. The fluid utilized by the instrument is for surface conduction correction measurements. These solutions were used both as supplied and with 7.4 pH buffer added to determine the streaming potential at physiologic fluid pH and to minimize pH drift. The surface conduction measurements were made to determine the effect of surface conduction on the measured zeta potential. For substrates treated at high polymer concentrations by the method of the current invention, the zeta potential measurements with surface conduction correction are significantly greater than without the correction, but the difference between these measurements decreases with polymer concentration on substrate. The data collected are tabulated as streaming potentials. Untreated cotton substrates have shown a typical zeta potential of −15 to −20 mV. Cotton substrates treated by the methods of this invention have been demonstrated to show zeta potential values above +15 mV. Rayon products show similar values. The corrected zeta potential of an untreated sample of rayon substrate under pH 7.4 buffered conditions was in the range of −10 mV, while the treated sample yielded values between +10 and +30 mV.

Samples of 100% knitted jersey material were prepared according to the method of Examples 3B. The concentration of polyDADMAC in the treatment solution was varied from zero to 1.90 wt %. Zeta potentials were measured as described above. The antimicrobial efficacy of the materials against *Staph. aureus* and *E. coli* was determined by the method described in Example 7. The results are shown below in Table 1.

EXAMPLE 7

Microbiological Assay to Verify the Antimicrobial Property of Treated Substrate Material.

Antimicrobial activity of materials prepared using the various methods and embodiments of this invention were assayed using a modified version of the American Association of Textile Chemists and Colorists (AATCC) Test Method 100 ("*Antibacterial Finishes on Textiles: Assessment of*"), a test designed to test antibacterial finishes of textile materials. Overnight cultures (ONC) of test microorganisms were generated in appropriate culture medium using standard methods. Using the ONC, an inoculum solution was prepared containing the test microorganism diluted to ~$10^6$ CFU/ml in phosphate buffered saline (PBS) and fetal bovine serum (FBS), at 10% v/v. Treated substrate materials (samples) and untreated substrate control materials (controls) were cut into 2.5 cm squares and autoclaved at 121° C. for 30 minutes to eliminate pre-existing microbial contamination. After autoclaving, samples and controls were allowed to cool for 15 minutes at room temperature. Samples and controls were each inoculated with 500 µL of inoculum and incubated at 37° C. in sterile covered petri dishes. After 24 hours incubation, the samples and controls were harvested with sterile forceps, placed into separate 15 mL tubes containing 15 mL PBS, and vortexed for 30 seconds to suspend any remaining viable microorganisms into solution. Appropriate tenfold dilutions of these suspensions were made using PBS solution and spread onto bacteria culture plates containing growth medium appropriate for the desired organisms and then incubated overnight at 37° C. After overnight culture, colonies growing on each plate are enumerated to determine antimicrobial efficacy. Data are reported as % killed or log reduction as compared to untreated controls. The dilution, spreading, plating and enumeration were conducted using standard microbiological techniques. Results of this testing on samples made using various embodiments of the described invention are presented in Table 3.

TABLE 1

Zeta Potential and Antimicrobial Efficacy of Treated Samples

| % pDADMAC in treatment solution | Zeta potential (mV) | Zeta potential with SCC (mV) | Log Reduction of S. aureus | Log Reduction of E. coli |
|---|---|---|---|---|
| 1.90% | 19.9 ± 0.8 | 27.9 ± 0.5 | 6.19 | 6.76 |
| 0.98% | 29.4 ± 0.3 | 33.5 ± 0.4 | 6.19 | 6.76 |
| 0.66% | 24.5 ± 1.9 | 28.2 ± 2.2 | 6.19 | 6.43 |
| 0.49% | 28.9 ± 0.2 | 35.2 ± 0.2 | 6.19 | 4.84 |
| 0.40% | 25.5 ± 0.3 | 29.1 ± 0.6 | 5.19 | 5.99 |
| 0.33% | 16.2 ± 0.4 | 18.5 ± 0.5 | 2.99 | 1.80 |
| 0.28% | 17.0 ± 0.2 | 19.7 ± 0.3 | 5.09 | 1.73 |
| 0.25% | 16.3 ± 0.1 | 19.2 ± 0.2 | 1.87 | 1.91 |
| 0.22% | 11.4 ± 0.2 | 13.8 ± 0.3 | 2.40 | 1.57 |
| 0.20% | 10.7 ± 0.3 | 12.5 ± 0.3 | 2.45 | 1.22 |
| 0.00% | 24.3 ± 1.7 | 34.1 ± 0.2 | 0.00 | 0.00 |

EXAMPLE 8

Microbiological Assay to Verify the Antimicrobial Property of a Treated Substrate was Non-Leachably Attached.

Materials prepared using the method of Example 3B, as well as untreated control materials were rinsed repeatedly to remove unbound antimicrobial cationic polyelectrolyte by the procedure described in Example 3B. Control and sample were cut into 120 sq-cm pieces. Four sample and four control pieces were placed into separate beakers containing 20 ml of 0.9% NaCl solution. Beakers were then placed in an oven at each of the following four conditions: 121° C. for 1 hour, 70° C. for 24 hours, 50° C. for 72 hours, or 37° C. for 120 hours. After the indicated amount of time, the beakers were removed from the oven and the extract solution from each beaker was harvested. The extract solutions were diluted to ¼ log, ½ log, ¾ log and 1 log. Bacteria culture plates were prepared by lawn-spreading a 1/100 dilution of an ONC of test microorganisms, both S. aureus and E. coli. After the culture medium had absorbed the inoculum, a 20 μl aliquot of each dilution of each extract solution was placed at marked locations on the plates. Bacterial culture plates were then incubated overnight at 37° C. and inspected for observed % kill and size of the zone of inhibition surrounding marked spots. No evidence of antimicrobial effect was observed at the marked locations, indicating the nonleachable character of the bound microbicide.

EXAMPLE 9

Treatment of a Nonwoven Rayon Fabric Substrate with Nonpolymeric Quaternary Ammonium Compounds (Comparative Example).

This example demonstrates the lack of non-leachable binding of a non-polymeric quaternary compound to a cotton substrate and/or lack of binding of antimicrobial non-polymeric quaternary compounds to a substrate. A woven 100% cotton gauze material was used (Kerlix™, manufactured by Kendall) was treated with the non-polymeric quaternary ammonium compounds listed below according to the following procedure. After the substrate was saturated with the solution (5% quaternary compound), the substrate was pressed free of excess solution. The wetted and pressed substrate was then placed into 80° C. drying oven for 2 hours, until the treated substrate was dried thoroughly. After thorough drying of the treated cotton substrate, it was washed twice in a large excess of 1% aqueous NaCl solution to remove any quaternary compound that did not become non-leachably attached to the substrate during the drying step. It was then rinsed repeatedly with water until conductivity readings of the rinsate equaled that of the input rinse water, indicating that the rinsate was free of quaternary compound. The following non-polymeric quaternary ammonium compounds were used:

| Sample # | compound |
| --- | --- |
| 9A | chlorhexidine |
| 9B | tetraethylammonium bromide |
| 9C | tetramethylammonium bromide |
| 9D | benzalkonium chloride |
| 9E | tetrabutylammonium bromide |
| 9F | didecyldimethylammonium chloride |

These treated materials were tested for antimicrobial efficacy according to the procedure given in Example 7 using *Pseudomonas aeruginosa* as the test organism. The antimicrobial efficacy for each sample is listed below:

| Sample # | log reduction |
| --- | --- |
| 9A | >6 |
| 9B | 0 |
| 9C | 0 |
| 9D | 2 |
| 9E | 5 |

Fresh portions of the three samples which showed antimicrobial activity (9A, 9D, and 9E) were subjected to extraction testing in order to determine leachability of the non-polymeric antimicrobials. The method of Example 8 was used, with the following modifications: Four grams of material was extracted into 20 mL of 1% NaCl (aq), for 24 hours at 70° C. Undiluted extracts were plated. Activity was observed for all three samples, indicating lack of non-leachable attachment of non-polymeric antimicrobial cationic polyelectrolyte. Note that this is in contrast to the behavior observed in Example 8 for quaternary antimicrobial cationic polyelectrolyte.

EXAMPLE 11

Treatment of Laboratory Filter Paper with Polymerized Diallyldimethylammonium Chloride.

A sample of laboratory filter paper (Whatman) was soaked in an aqueous solution of 1 wt % polymerized diallyldimethylammonium chloride. After the filter paper substrate was saturated, it was placed into an 80° C. drying oven for two hours, until the treated rayon substrate was dried thoroughly.

After drying, the treated filter paper sample was rinsed three times in deionized water and dried again at 80° C. in the manner described above. A portion of this treated substrate was retained and hereafter is referred to as Sample 1. Another portion was rinsed two times with 1% sodium chloride solution, followed by three additional rinses with deionized water, then dried again at 80° C. for two hours. A portion of this treated substrate was retained and hereafter is referred to as Sample 2.

Portions of Samples 1 and 2 were soaked in a solution 0.5% BTB indicator adjusted to pH>20 and rinsed repeatedly with deionized water. A uniform medium blue color, indicative of quaternary ammonium groups bonded to the paper surface, was imparted to the paper and was not diminished by further rinsing or soaking in water. An untreated filter paper control was also subjected to the dye test. The untreated filter paper remained slightly blue at first, however, the blue color leached out after soaking in distilled water overnight, and the paper became white.

EXAMPLE 12

Treatment of Cornstarch with Polymerized Diallyldimethylammonium Chloride.

Fifty grams of cornstarch (Argo) was mixed with 50 mL of a 1 wt % aqueous solution of polymerized diallyldimethylammonium chloride. The mixture was then spread on a pan and allowed to dry at room temperature overnight and then was dried thoroughly in an oven at 80° C. for two hours. The treated cornstarch was then ground to a powder consistency and rinsed several times with distilled water. Centrifugation was used to assist in the recovery of the treated cornstarch powder between rinsings. After rinsing, the powder was allowed to dry at room temperature overnight and then was dried thoroughly in an oven at 80° C. for two hours. The treated and rinsed cornstarch was then ground to a powder consistency.

A BTB dye test was performed using the method described in Example 5. The treated cornstarch showed a distinct blue color, compared with untreated starch, which was only a very pale blue.

The antimicrobial activity of both rinsed and un-rinsed cornstarch powder was assayed by the ability of bacteria cultures to grow in suspension in the presence treated and untreated cornstarch. Treated sample and untreated control cornstarch material (0.5 g) was placed into of solution of 9 ml of phosphate buffered saline and 1 ml of a ten-fold dilution of ONC of bacteria. Sample and control were shaken on shaker at 37° C. for the indicated amount of time. Sample and control were then serially diluted and the dilutions were streaked onto bacterial culture plates. After overnight culture at 37° C., colonies growing on each plate were enumerated. The results are shown in Table 2 below:

TABLE 2

| Time shaken | Log Reduction | | Untreated controls |
|---|---|---|---|
| (min) | Rinsed samples | Unrinsed samples | CFU/mL |
| 10 | 3.76 | 6.91* | 8.10E+06 |
| 30 | 4.18 | 6.65* | 4.50E+06 |
| 60 | 4.78 | 6.48* | 3.00E+06 |
| 120 | 5.04 | 6.74* | 5.50E+06 |

*= Complete kill (100%)

EXAMPLE 13

The Following Example Demonstrates the Preparation and Properties of Materials Containing Non-Leachable Bound Antimicrobials Prepared using Various Polymeric Antimicrobials.

The method of Example 3B was used; however, the following quaternary ammonium polymers were used: polyDADMAC; Poly(vinylbenzyl ammonium chloride)—otherwise known as pVBTAC; poly(2-(methacryloyloxy)ethyl) trimethylammonium chloride)—otherwise known as pTMMC; poly(dimethylaminoethyl methacrylate hydrochloride)—otherwise known as p(DMAEMA). Each polymer was synthesized from the corresponding monomer in aqueous solution using free radical initiators. All polymers were applied to the substrates as 5 wt % aqueous solutions. Antimicrobial efficacy was determined by the method described in Example 7. Results are presented in the following table.

| Sample | log reduction of *Pseudomonas aeruginosa* |
|---|---|
| pDADMAC | 6 |
| pVBTAC | 5 |

-continued

| Sample | log reduction of *Pseudomonas aeruginosa* |
|---|---|
| pTMMC | 1 |
| pDMAEMA | 1 |

EXAMPLE 14

Assessment of Effect of Drying Step on Non-Leachable Attachment of Polymeric Antimicrobial to a Cotton Substrate.

A woven 100% cotton gauze material was used as a substrate (Kerlix™, manufactured by Kendall). This substrate was treated with a 5% solution of polyDADMAC. Drying was conducted in a sealed plastic chamber equipped with a humidity measuring apparatus (Fisher Scientific model # 11-661-18). Samples were left in the chamber at specified humidity (% relative humidity) for a period of approximately 24 hours. Humidity was controlled by placing an appropriate amount of wet paper towels on the floor of the plastic chamber. Samples were suspended on a screen in the center of the chamber, approximately 1.5" above the floor. Samples were "dried" at room temperature. After removal from the humidity chamber, samples were immediately washed according to the procedure of Example 3B. Samples were then tested for antimicrobial efficacy according to the procedure of Example 7. Results are presented below:

| Sample | log reduction of *Pseudomonas aeruginosa* |
|---|---|
| 30% rh | 8 |
| 45% rh | 8 |
| 70% rh | 6 |
| 90% rh | 6 |
| 100% rh | 2 |

The degree of dryness of the samples would be expected to be dependent on the relative humidity of the air within the drying chamber. Thus, the positive effect of thorough drying on non-leachable bonding of polymeric quaternary antimicrobial is demonstrated.

EXAMPLE 15

Preparation of Materials with Non-Leachable Bound Antimicrobials.

Materials were prepared according to the method of Example 3B, except that various substrates and polyDADMAC concentrations were used (as indicated below). The products with non-leachably attached antimicrobial polymer were tested for antimicrobial activity as described in Example 7. The organisms tested, and the antimicrobial activity in terms of log-reduction of viable organisms is presented below:

| Assay # | Substrate | Organism | Treatment | Avg. LR | Full kill (y/n) |
|---|---|---|---|---|---|
| 275 | Kerlix Cotton Gauze | SA | 10% PD | 7.00 | Y |
| 336 | Knitted Cotton Jersey | SA | 0.30% PD | 7.34 | Y |
| 321 | Rayon Wound Pad | SA | 5% PD | 6.75 | Y |
| 321 | Cotton Wound Pad | SA | 5% PD | 6.91 | Y |
| 272 | 55% Cotton/45% PET | SA | 1.0% PD | 6.81 | Y |
| 217 | Bulk cotton | SA | 2.0% PD | 7.03 | Y |
| 217 | Wood pulp | SA | 2.5% PD | 7.03 | Y |
| 210 | Cotton Socks | SA | 1.0% PD | 6.96 | Y |
| 169 | Bulk Rayon Staple | SA | 1.25% PD | 5.37 | N |
| 208 | Kerlix Cotton Gauze | SE | 10% PD | 7.44 | Y |
| 84 | Knitted Cotton Jersey | SE | 0.74% PD | 6.81 | Y |
| 275 | Kerlix Cotton Gauze | EC | 10% PD | 7.00 | Y |
| 258 | Knitted Cotton Jersey | EC | 1.2% PD | 7.11 | Y |
| 110 | Cotton Socks | EC | 1.1% PD | 7.53 | Y |
| 196 | Cotton Gauze | EC | 4.0% | 6.50 | Y |
| 169 | Bulk Rayon Staple | EC | 1.25% PD | 4.73 | N |
| 275 | Kerlix Cotton Gauze | PA | 10% PD | 7.00 | Y |
| 330 | Jersey Material | PA | >1% PD | 7.0 | Y |
| 321 | Cotton Wound Pad | PA | 5% PD | 7.57 | Y |
| 272 | 55% Cotton/45% PET | PA | 1.0% PD | 5.32 | N |
| 225 | Wood pulp | PA | 5.0% PD | 4.79 | N |
| 217 | Bulk cotton | PA | 2.0% PD | 7.21 | Y |
| 227 | Kerlix Cotton Gauze | SP1 | 5% PD | 5.81 | Y |
| 65 | Bulk cotton | SP1 | 5% PD | 5.84 | N |
| 227 | Kerlix Cotton Gauze | PV | 5% PD | 7.53 | Y |
| 65 | Bulk cotton | PV | 5% PD | 3.65 | N |
| 59 | Wood pulp | PV | 1.25% PD | 6.56 | Y |
| 309 | Kerlix Cotton Gauze | PM | 10% PD | 6.71 | Y |
| 208 | Kerlix Cotton Gauze | EF | 5% PD | 7.06 | Y |
| 208 | Kerlix Cotton Gauze | EA | 10% PD | 5.88 | N |
| B 0805 | Kerlix Cotton Gauze | MRSA | 2% PD | 6.06 | N |
| 280 | 55% Cotton/45% PET | MRSA | ~1.0% PD | 6.47 | Y |
| B0805 | Kerlix Cotton Gauze | VRE | 2% PD | 5.20 | N |
| B 0805 | Kerlix Cotton Gauze | LM | 2% PD | 7.54 | Y |
| 161 | Knitted Cotton Jersey | LM | ~0.7% PD | 6.85 | Y |
| 59 | Wood pulp | LM | 1.25% PD | 6.65 | Y |
| 271 | Kerlix Cotton Gauze | CX | 10% PD | 5.68 | N |
| 192 | Cotton Socks | CX | ~1.6% PD | 5.85 | Y |
| 177 | Knitted Cotton Jersey | CX | ~0.7% PD | 6.00 | Y |
| 271 | Kerlix Cotton Gauze | ML | 10% PD | 6.02 | Y |
| 192 | Cotton Socks | ML | ~1.6% PD | 6.31 | Y |
| 174 | Knitted Cotton Jersey | ML | ~0.7% | 5.70 | Y |
| 169 | Bulk Rayon Staple | ML | ~1.25% PD | 4.05 | Y |
| 84 | Knitted Cotton Jersey | CD | ~0.74% PD | 6.26 | Y |
| 345 | Kerlix Cotton Gauze | SM | 10% PD | 6.76 | Y |
| 291 | Kerlix Cotton Gauze | KP | 10% PD | 7.35 | Y |
| 65 | Bulk cotton | KP | 5% PD | 7.11 | Y |
| 51 | Knitted Cotton Jersey | KP | 5% PD | 6.06 | Y |
| 59 | Wood pulp | SC | 1.25% PD | 6.67 | Y |

Key:
Assay # = internal reference number
PD = polyDADMAC
Avg. LR = Log Reduction
Full Kill (y/n) = Yes or No
Organism:
SA = *Staphylococcus aureus* ATCC # 6538
SE = *Staphylococcus epidermidis* ATCC # 12228
EC = *Escherchia coli* ATCC # 15597
PA = *Pseudomonas aeruginosa* ATCC # 15442
SP = *Streptococcus pyogenes* ATCC # 10096
PV = *Proteus vulgaris* ATCC # 29905
PM = *Proteus mirabilis* ATCC # 7003
EF = *Enterococcus faecalis* ATCC # 10741
EA = *Enterobacter aerogenes* ATCC # 13048
MRSA = Methicillan resistant *S. aureus* ATCC # BAA-44
VRE = Vancomycin resistant *E. faecium* ATCC # 700221
LM = *Listeria monocytogenes* ATCC # 13932
CX = *Corynebacterium xerosis* ATCC # 7711
ML = *Micrococcus luteus* ATCC # 21102
CD = *Corynebacterium diptheriae* ATCC # 43145
SM = *Serratia marcescens* ATCC # 13880
KP = *Klebsiella pneumoniae* ATCC # 13883
SC = *Salmonella choleraesuis* ATCC # 10708

EXAMPLE 16

A Comparative Example Demonstrating the Preparation and Antimicrobial Efficacy of Materials Prepared by the Method of Batich (U.S. 020177828 A1) (Comparative Example).

A free-radical initiated graft polymerization of DADMAC monomer onto a cotton substrate (Kerlix cotton gauze) was carried out according to the method of Batich et al. Substrates were immersed in an excess of aqueous solutions containing DADMAC monomer and sodium persulfate initiator (0.9 wt %). Solutions were sparged thoroughly with argon gas, then sealed and heated at 60° to 80° C. for at least 4 hours, followed by thorough rinsing as described in Example 3B to remove unbonded and leachable antimicrobial polymer. The samples were tested for antimicrobial activity according to the procedure described in Example 7. The test organism was *Pseudomonas aeruginosa*. Results are summarized below:

| DADMAC conc. | Average log reduction |
|---|---|
| 12% | −0.28 |
| 23% | 1.58 |
| 35% | 4.27 |
| 47% | 5.05 |
| 59% | 5.72 |

Comparison with the antimicrobial efficacy of the current invention (as shown in Example 15) demonstrates that the current invention is capable of producing a non-leachable antimicrobial material with greater efficacy than that provided by the prior art, even when substantially lower concentrations of antimicrobial agent are used. Furthermore, this can be accomplished without the need for conducting the treatment in an inert atmosphere.

EXAMPLE 17

Health & Safety Testing of a Cotton Wound Dressing Material Containing a Non-Leachable Antimicrobial Polymer.

Materials prepared according to the method of Example 3B (substrate was Kerlix cotton gauze, and [polyDADMAC] was 5%) were submitted for safety testing at Toxikon Laboratories, Bedford, Mass. Cytotoxicity, Sensitization, Intracutaneous Reactivity, and Acute Systemic Toxicity Tests were performed. Such testing is required by regulatory agencies such as the FDA before materials such as antimicrobial wound dressings can be approved for sale and use. The material passed all the tests with lowest (best) possible scores on every test.

Agar diffusion test, ISO 10993-5, 1999. This test is also referred to as a Cytotoxicity test. The material was found to elicit no response from the L929 mammalian cell line at 48 hours post exposure to the test article: a grade 0 response was found at all time points. The material was determined by Toxikon labs to pass this test.

Intracutaneous Injection Test, ISO 10993-10, 2002. The extracts from the material were found to elicit no significantly greater biological reaction than extracts from negative control articles when tested on New Zealand white rabbits. No signs of toxic response were found at any time point, and there was zero incidence of erythema/eschar and zero incidence of edema, using either for NaCl extract media, or for cottonseed oil extract media. The material was determined by Toxikon labs to pass this test.

Kligman Maximization Test (also known as sensitization), ISO 10993-10993-10, 2002. The material extract elicited no reaction at the challenge (0% sensitization), following the induction phase. There were no readings of toxicity, and the scores for all the test animals at all test time points were 0. As defined by the scoring system of Kligman, this is categorized as a grade I reaction, and the test article is classified as having weak allergenic potential. The Grade I sensitization is not considered significant according to this test. The material was determined by Toxikon labs to pass this test.

Systemic Injection Test, ISO 10993-11, 1993. The material was found to elicit no significantly greater biological reaction than treated with control articles when tested on Albino Swiss mice. No signs of toxic response were found at any time point. The material was determined by Toxikon labs to pass this test.

EXAMPLE 18

Determination of Non-Leaching Antimicrobial Polymer Content of Treated Materials.

Materials were prepared according to the method of Example 3B using Kerlix cotton gauze as the substrate, and varying the concentration of polyDADMAC in the treatment solution, as indicated in the table below. Elemental analysis for nitrogen content (Kjelldahl method) was performed by Galbraith Laboratories in Knoxville, Tenn., and is reported as ppm (see table below). Based on the nitrogen content, the % of polyDADMAC remaining in the product as a non-leachably attached polymeric antimicrobial was calculated by using the formula weight of DADMAC, and subtracting the nitrogen content of the untreated materials.

| % pDADMAC (treatment) | Nitrogen (ppm) | % PD (product) |
|---|---|---|
| 0.00% | 158 | 0.00% |
| 0.00% | 120 | 0.00% |
| 0.55% | 252 | 0.13% |
| 1.10% | 312 | 0.20% |
| 2.36% | 390 | 0.29% |
| 3.99% | 520 | 0.44% |
| 10.00% | 598 | 0.53% |

EXAMPLE 19

Demonstration of Retention of Antimicrobial Efficacy of Inherently Antimicrobial Material after Fifty Laundering Cycles.

A sample was prepared according to the procedure of example 3A, except that the treatment solution consisted of 1% polyDADMAC in water. After drying, the product was laundered according to AATCC standard method #135-2110 (*Dimensional Changes in Automatic Home Laundering of Woven and Knit Fabrics*) to achieve the equivalent of 50 home laundering cycles. The material was then tested for antimicrobial efficacy according to the method of Example 7, and found to give a 6.6 log reduction of *Staph aureus*, indicating retention of appreciable inherent antimicrobial activity, even after fifty laundering cycles. The laundering treatment was performed by Textile Testing Service, University of Manitoba (Manitoba, Canada).

EXAMPLE 20

Comparative Example.

Samples of bulk cotton material were treated according to the method of Onabe ("*Studies of Interfacial Properties of Polyelectrolyte-Cellulose Systems. I. Formation and Structure of Adsorbed layers of Catioinic Polyelectrolyte-(Poly-DMDAAC) on Cellulose Fibers" Journal of Applied Polymer Science*, Vol. 22, 3495-3510 (1978). Cotton samples (0.4 grams each) were immersed in separate 40 mL portions of 2% polyDADMAC solution. Samples were left to soak for either 24 hours, or for approximately 5 minutes. Samples for each soaking time were then thoroughly dried (according to the method of the current invention, but distinct from the method of Onabe). These dried samples, along with duplicate samples subjected to the same soaking conditions described above, were then rinsed according to the method of Onabe. Specifically, each sample was placed into a glass filter and rinsed with 1 liter of deionized water, then transferred to a glass beaker filled with 200 mL of distilled water, and allowed to stand overnight. The electrical conductivity of the water in each beaker was then measured, with the flowing results:

24 hour/rinsed: 875
24 hour/dried & rinsed: 4
5 minute/rinsed: 8
5 minute/dried & rinsed: 3

The conductivity of the solution is reflective of the concentration of polyDADMAC in solution, and indicates two things. First, drying prior to rinsing has a pronounced effect, causing a significant reduction in the amount of polyDADMAC leaching (leaving the cotton and migrating into solution). Second, it appears that the longer soaking time results in greater absorption of polyDADMAC into the wet cellulose fiber, however, this greater amount is subsequently lost during rinsing, if the rinsing is done prior to drying the sample.

The samples were then thoroughly dried and subjected to the dye test described in Example 5, and then photographed. The results of the dye testing were that both non-dried rinsed samples showed only a Light Blue color, indicative of relatively low, if any, antimicrobial efficacy. Both of the samples subjected to a drying step prior to rinsing showed a Dark Blue color, indicative of high antimicrobial efficacy.

We claim:

1. A method of imparting non-leachable antimicrobial properties to a substrate consisting essentially of, in sequence, the steps of:
   a) providing a substrate for use in textiles, medical applications, filters, absorbent materials, or packaging materials, comprised in whole or in part of a cellulosic material,
   b) treating the substrate by applying an aqueous solution of an antimicrobial cationic polyelectrolyte to the substrate comprised in whole or in part of a cellulosic material wherein the antimicrobial cationic polyelectrolyte has an average degree of polymerization of at least 3, and an excess cationic charge density of at least 1 mole per 25,000 grams; wherein the solution concentration of the antimicrobial cationic polyelectrolyte is at least 0.01 weight percent,
   c) thoroughly drying the treated substrate,
   d) rinsing, washing, or extracting to remove any leachable unbonded portion of said antimicrobial cationic polyelectrolyte, and
   e) performing an assay to verify that non-leachable antimicrobial properties have been imparted to said substrate,
   whereby non-leachable bonding is effected between at least a portion of the antimicrobial cationic polyelectrolyte and the substrate comprised in whole or in part of a cellulosic material.

2. The method of claim 1 wherein said antimicrobial cationic polyelectrolyte has an average degree of polymerization of from 20 to 10,000.

3. The method of claim 1 wherein said antimicrobial cationic polyelectrolyte has a minimum excess cationic charge density of at least 1 mole per 162 grams of antimicrobial cationic polyelectrolyte.

4. The method of claim 1 wherein said antimicrobial cationic polyelectrolyte has a minimum excess cationic charge density of at least 1 mole per 212 grams of antimicrobial cationic polyelectrolyte.

5. The method of claim 1 wherein said antimicrobial cationic polyelectrolyte is an ammonium compound.

6. The method of claim 1 wherein the solution concentration of antimicrobial cationic polyelectrolyte is between 0.05 and 5 weight percent.

7. The method of claim 1 wherein thorough drying is accomplished by application of infrared heat, radiant heat, or hot air.

8. The method of claim 1, wherein said assay to verify that non-leachable antimicrobial properties have been imparted to said substrate is selected from the group consisting of:
   a dye assay utilizing a negatively-charged dye molecule;
   measurement of zeta potential;
   a microbiological assay.

9. The method of claim 1 wherein said antimicrobial cationic polyelectrolyte comprises polyDADMAC homopolymer or poly(vinylbenzyltrimethylammonium chloride) homopolymer.

10. The method of claim 9 wherein said polyDADMAC homopolymer or poly(vinylbenzyltrimethylammonium chloride) homopolymer has an average degree of polymerization of from 100 to 2,500.

11. The method of claim 9 wherein the solution concentration of polyDADMAC homopolymer or poly(vinylbenzyltrimethylammonium chloride) homopolymer is between 0.05 and 5 weight percent.

12. The method of claim 1 wherein the substrate comprised in whole or in part of a cellulosic material is gauze, a wound dressing, or a component of a wound dressing.

13. A method of imparting non-leachable antimicrobial properties to an absorbent material consisting essentially of, in sequence, the steps of:
   a) providing an absorbent substrate for use in textiles, medical applications, filters, absorbent materials, or packaging materials, comprised in whole or in part of cotton,
   b) treating the absorbent substrate by applying an aqueous solution comprising polyDADMAC homopolymer or poly(vinylbenzyltrimethylammonium chloride) homopolymer to the absorbent substrate comprised in whole or in part of cotton wherein the polyDADMAC homopolymer or poly(vinylbenzyltrimethylammonium chloride) homopolymer has an average degree of polymerization of at least 3, and an excess cationic charge density of at least 1 mole per 212 grams: wherein the solution concentration of polyDADMAC homopolymer or poly(vinylbenzyltrimethylammonium chloride) homopolymer is at leas 0.01 weight percent,
   c) thoroughly drying the treated absorbent substrate,
   d) rinsing the treated absorbent substrate to remove any leachable unbonded portion of said polyDADMAC homopolymer or poly(vinylbenzyltrimethylammonium chloride) homopolymer, and e) performing an assay to verify that non-leachable antimicrobial properties have been imparted to said substrate, whereby non-leachable bonding is effected between at least a portion of the polyDADMAC homopolymer or poly(vinylbenzyltrimethylammonium chloride) homopolymer and the substrate comprised in whole or in part of cotton.

14. The method of claim 13, wherein said assay to verify that non-leachable antimicrobial properties have been imparted to said substrate is selected from the group consisting of:
a dye assay utilizing a negatively-charged dye molecule;
measurement of zeta potential;
a microbiological assay.

15. The method of claim 13 wherein said polyDADMAC homopolymer or poly(vinylbenzyltrimethylammonium chloride) homopolymer has an average degree of polymerization of from 100 to 2,500.

16. The method of claim 13 wherein the solution concentration of polyDADMAC homopolymer or poly(vinylbenzyltrimethylammonium chloride) homopolymer is between 0.05 and 5 weight percent.

17. The method of claim 13 wherein thorough drying is accomplished by application of infrared heat, radiant heat, or hot air.

18. The method of claim 13 wherein the substrate comprised in whole or in part of cotton is gauze, a wound dressing, or a component of a wound dressing.

19. The method of claim 13 wherein the absorbent substrate is used in textiles.

20. The method of claim 13 wherein the substrate comprises in whole, or in part, gauze, a wound dressing, or a component of a wound dressing.

21. A method of attaching an antimicrobial cationic polyelectrolyte to a substrate for use in textiles, medical applications, filters, absorbent materials, or packaging material, wherein said substrate is comprised in whole or in part of hydroxyethyl cellulose, carboxymethyl cellulose, methyl cellulose, polysaccharide, gelatin, chitin, chitosan, alginate, starch, collagen, polyglycolide, polylactide, polyamide, polyurethane, rubber, polyester, acrylic, nylon, rayon, silk, linen, cotton, wool, woven flexible material, fabric, protein, collagen, or absorbent materials for aqueous fluids, and wherein said antimicrobial cationic polyelectrolyte is not self-crosslinking and has an average degree of polymerization of at least 3, wherein said method consists essentially of, in sequence, the steps of wetting the substrate with an aqueous solution of the antimicrobial cationic polyelectrolyte followed by drying of the wetted substrate, wherein said drying causes at least a portion of the antimicrobial cationic polyelectrolyte to become attached to the substrate in a non-leachable manner, and further comprises rinsing, washing, or extracting to remove any leachable unbonded portion of said antimicrobial cationic polyelectrolyte from said substrate, wherein said rinsing, washing, or extracting occurs immediately after drying of the wetted substrate, wherein an assay is performed to verify that non-leachable antimicrobial properties have been imparted to said substrate, and wherein the attached antimicrobial cationic polyelectrolyte provides non-leaching antimicrobial activity to the resulting product.

22. The method of claim 21 wherein drying is accomplished by application of infrared heat, radiant heat, or hot air.

23. The method of claim 21 wherein the substrate is comprised in whole or in part of cotton, and wherein the antimicrobial cationic polyelectrolyte that is not self crosslinking comprises polyDADMAC homopolymer having an excess cationic charge density of at least 1 mole per 162 grams or poly(vinylbenzyltrimethylammonium chloride) homopolymer having an excess cationic charge density of at least 1 mole per 212 grams; and wherein the solution concentration of polyDADMAC homopolymer or poly(vinylbenzyltrimethylammonium chloride) homopolymer is at least 0.01 weight percent.

24. The method of claim 23 wherein said polyDADMAC homopolymer or poly(vinylbenzyltrimethylammonium chloride) homopolymer has an average degree of polymerization of from 100 to 2,500.

25. The method of claim 23 wherein the solution concentration of polyDADMAC homopolymer or poly(vinylbenzyltrimethylammonium chloride) homopolymer is between 0.05 and 5 weight percent.

26. The method of claim 21, wherein said assay to verify that non-leachable antimicrobial properties have been imparted to said substrate is selected from the group consisting of:
a dye assay utilizing a negatively-charged dye molecule;
measurement of zeta potential;
a microbiological assay.

27. The method of claim 21 wherein said antimicrobial cationic polyelectrolyte has an average degree of polymerization of from 100 to 2,500.

28. The method of claim 21 wherein the solution concentration of antimicrobial cationic polyelectrolyte is between 0.05 and 5 weight percent.

29. The method of claim 21 wherein drying is accomplished by application of infrared heat, radiant heat, or hot air.

30. The method of claim 21 wherein the substrate comprised in whole or in part of a cellulosic material is gauze, a wound dressing, or a component of a wound dressing.

31. The method of claim 21 wherein the substrate comprises in whole, or in part, a fabric or a textile.

\* \* \* \* \*